United States Patent
Cochran et al.

(12) 
(10) Patent No.: US 6,759,535 B2
(45) Date of Patent: Jul. 6, 2004

(54) INHIBITORS OF P38

(75) Inventors: John Cochran, Marshfield, MA (US); Roger Tung, San Diego, CA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 73 days.

(21) Appl. No.: 10/400,269

(22) Filed: Mar. 25, 2003

(65) Prior Publication Data

US 2003/0203905 A1 Oct. 30, 2003

Related U.S. Application Data

(62) Division of application No. 10/171,017, filed on Jun. 11, 2002, now Pat. No. 6,552,019.
(60) Provisional application No. 60/297,426, filed on Jun. 11, 2001.

(51) Int. Cl.$^7$ .................... C07D 217/16; C07F 9/06
(52) U.S. Cl. .................... 546/23; 546/143; 546/144
(58) Field of Search ............... 546/23, 143, 144

(56) References Cited

U.S. PATENT DOCUMENTS 6,248,738 B1 * 6/2001 Dickinson et al. ....... 514/235.2

FOREIGN PATENT DOCUMENTS

WO    WO 99/58502    11/1999
WO    WO 99/64400    12/1999

* cited by examiner

*Primary Examiner*—Joseph K. McKane
*Assistant Examiner*—Golam M M Shameem
(74) *Attorney, Agent, or Firm*—Fish & Neave; James F. Haley, Jr.; Denise Bergin

(57) ABSTRACT

The present invention relates to inhibitors of p38, a mammalian protein kinase involved cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

1 Claim, No Drawings

INHIBITORS OF P38

This application is a division of U.S. patent application Ser. No. 10/171,017, filed Jun. 11, 2002, now U.S. Pat. No. 6,552,019, which claims the benefit of U.S. Provisional Patent Application No. 60/297,426, filed Jun. 11, 2001.

TECHNICAL FIELD OF INVENTION

The present invention relates to inhibitors of p38, a mammalian protein kinase involved in cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

BACKGROUND OF THE INVENTION

Protein kinases are involved in various cellular responses to extracellular signals. Recently, a family of mitogen-activated protein kinases (MAPK) has been discovered. Members of this family are Ser/Thr kinases that activate their substrates by phosphorylation [B. Stein et al., Ann. Rep. Med. Chem., 31, pp. 289–98 (1996)]. MAPKs are themselves activated by a variety of signals including growth factors, cytokines, UV radiation, and stress-inducing agents.

One particularly interesting MAPK is p38. p38, also known as cytokine suppressive anti-inflammatory drug binding protein (CSBP) and RK, was isolated from murine pre-B cells that were transfected with the lipopolysaccharide (LPS) receptor, CD14, and induced with LPS. p38 has since been isolated and sequenced, as has the cDNA encoding it in humans and mouse. Activation of p38 has been observed in cells stimulated by stress, such as treatment of lipopolysaccharides (LPS), UV, anisomycin, or osmotic shock, and by cytokines, such as IL-1 and TNF.

Inhibition of p38 kinase leads to a blockade on the production of both IL-1 and TNF. IL-1 and TNF stimulate the production of other proinflammatory cytokines such as IL-6 and IL-8 and have been implicated in acute and chronic inflammatory diseases and in post-menopausal osteoporosis [R. B. Kimble et al., Endocrinol., 136, pp. 3054–61 (1995)].

Based upon this finding, it is believed that p38, along with other MAPKs, have a role in mediating cellular response to inflammatory stimuli, such as leukocyte accumulation, macrophage/monocyte activation, tissue resorption, fever, acute phase responses and neutrophilia. In addition, MAPKs, such as p38, have been implicated in cancer, thrombin-induced platelet aggregation, immunodeficiency disorders, autoimmune diseases, cell death, allergies, osteoporosis and neurodegenerative disorders. Inhibitors of p38 have also been implicated in the area of pain management through inhibition of prostaglandin endoperoxide synthase-2 induction. Other diseases associated with IL-1, IL-6, IL-8 or TNF overproduction are set forth in WO 96/21654.

Others have already begun trying to develop drugs that specifically inhibit MAPKs. For example, PCT publication WO 95/31451 describes pyrazole compounds that inhibit MAPKs, and, in particular, p38. However, the efficacy of these inhibitors in vivo is still being investigated.

Other p38 inhibitors have been produced, including those described in WO 98/27098, WO 99/00357, WO 99/10291, WO 99/58502, WO 99/64400, WO 00/17175 and WO 00/17204.

Accordingly, there is still a great need to develop new potent inhibitors of p38, including p38-specific inhibitors, that are useful in treating various conditions associated with p38 activation.

SUMMARY OF THE INVENTION

The present invention addresses this need by providing compounds, and pharmaceutically acceptable derivatives thereof, that demonstrate strong inhibition of p38. These compounds can be used alone or in combination with other therapeutic or prophylactic agents.

It is a principal object of this invention to provide novel classes of compounds which are inhibitors of p38. These compounds have the general formulae:

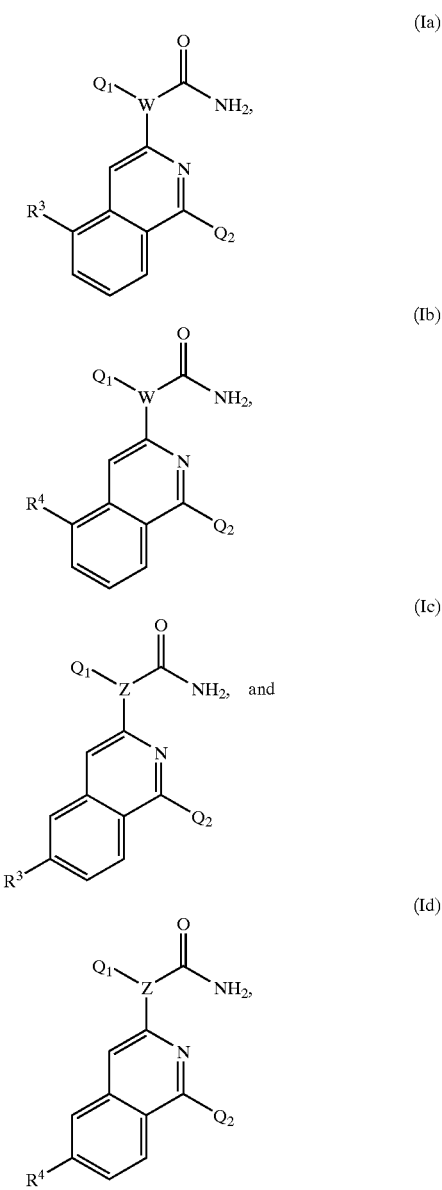

wherein each of $Q_1$ and $Q_2$ are independently selected from a phenyl or 5–6 membered aromatic heterocyclic ring system, or an 8–14 membered saturated, partially unsaturated, or aromatic bicyclic or tricyclic ring system containing 0–4 heteroatoms.

The rings that make up $Q_1$ are substituted with 1 to 4 substituents, each of which is independently selected from halo; C₁–C₃ aliphatic optionally substituted with halo, R', N(R')₂, OR', CO₂R' or CON(R')₂; O—(C₁–C₃)-aliphatic optionally substituted with halo, R', N(R')₂, OR', CO₂R' or CON(R')₂; R'; N(R')₂; OCF₃; CF₃; NO₂; CO₂R'; CON(R')₂; SR'; S(O₂)N(R')₂; SCF₃; CN; N(R')C(O)R⁴; N(R')C(O)OR⁴; N(R')C(O)C(O)R⁴; N(R')S(O₂)R⁴; N(R')R⁴; N(R⁴)₂; OR⁴; OC(O)R⁴; OP(O)₃H₂; N=CR'—N(R')₂; SO₂R'; or C(O)R'.

The rings that make up Q₂ are optionally substituted with up to 4 substituents, each of which is independently selected from halo; C₁–C₃ aliphatic optionally substituted with halo, R', N(R')₂, OR', CO₂R', S(O₂)N(R')₂, N=CR'—N(R')₂, R³, O—P(O₃)H₂, or CON(R')₂; O—(C₁–C₃)-aliphatic optionally substituted with halo, R', N(R')₂, OR', CO₂R', S(O₂)N (R')₂, N=CR'—N(R')₂, R³, OP(O₃)H₂, or CON(R')₂; R'; N(R')₂; OCF₃; CF₃; NO₂; CO₂R'; CON(R')₂; R³; OR³; N(R³)₂; SR³; C(O)R³; C(O)N(R')R³; C(O)OR³; SR'; S(O₂)N(R')₂; SCF₃; N=CR'—N(R')₂; R⁴; O—CO₂R⁴; N(R')C(O)R⁴; N(R')C(O)OR⁴; N(R')C(O)C(O)R⁴; N(R')S(O₂)R⁴; N(R')R⁴; N(R⁴)₂; OR⁴; OC(O)R⁴; OP(O)₃H₂; or CN.

Each R' is independently selected from hydrogen; (C₁–C₃)-aliphatic; phenyl or phenyl substituted with 1 to 3 substituents independently selected from halo, methoxy, cyano, nitro, amino, hydroxy, methyl or ethyl; or a 5–8 membered heterocyclic ring system optionally substituted with 1 to 3 substituents independently selected from halo, methoxy, cyano, nitro, amino, hydroxy, methyl or ethyl.

Each R³ is independently selected from a 5–8 membered aromatic or non-aromatic carbocyclic or heterocyclic ring system each optionally substituted with halo, R', R⁴, —C(O)R', —C(O)R⁴, —C(O)OR⁴, —J or —K; or an 8–10 membered saturated, partially unsaturated, or aromatic bicyclic ring system containing 0–4 heteroatoms, said ring system optionally substituted with halo, R', R⁴, —C(O)R', —C(O)R⁴, —C(O)OR⁴, —J or —K.

Each R⁴ is independently selected from —N(R')₂; —NR'C(O)—(C₁–C₄)-aliphatic optionally substituted with halo, R', N(R')₂, OR', CO₂R', CON(R')₂, SO₂N(R')₂, SO₂N(R⁵)₂, —J or —K; —NR'—(C₁–C₄)-aliphatic substituted with halo, R', N(R')₂, OR', CO₂R', CON(R')₂, SO₂N(R')₂, SO₂N(R')₂, —J or —K; —OC(O)—N(R')₂; a (C₁–C₄)-aliphatic, wherein up to two saturated carbon atoms of the aliphatic chain are each optionally and independently replaced by —C(O)—, —C(O)NR'—, —C(O)NR'NR'—, —CO₂—, —NR°C.(O)NR'—, —OC(O)—, —C(O)C(O)—, —OC(O)NR'—, —NR'NR'—, —NR'CO—, —NR'O—, —O—, —S—, —SO—, —SO₂—, —NR'—, —SO₂NR'—, —NR'SO₂—, and wherein the aliphatic chain is optionally substituted with halo, R', N(R')₂, OR', CO₂R', CON(R')₂, SO₂N(R')₂, SO₂N(R⁵)₂, —J or —K; a (C₁–C₇)-aliphatic optionally substituted with halo, R', N(R')₂, OR', CO₂R', CON(R')₂, SO₂N(R')₂, SO₂N(R⁵)₂, —J or —K; —J; —K; or a 5–6 membered aromatic or non-aromatic carbocyclic or heterocyclic ring system optionally substituted with halo, R', N(R')₂, OR', CO₂R', C(O)N(R')₂, SO₂N(R')₂ SO₂N(R⁵)₂, —J or —K.

R⁵ is selected from hydrogen; a (C₁–C₃)-aliphatic optionally substituted with halo, —R', —N(R')₂, —OR', SR', —C(O)N(R')₂, —S(O)₂N(R')₂, —C(O)OR', —N(R')S(O)₂(R'), —N(R')SO₂R⁶, —C(O)N(R')(R⁶), —N(R')C(O)R', —N(R')(R⁶), —C(O)R⁶, —C(O)N=C(NHR')₂ or R⁶.

R⁶ is selected from 5–8 membered aromatic or non-aromatic carbocyclic or heterocyclic ring systems each optionally substituted with halo, R', —C(O)R' or —C(O)OR'; or an 8–10 membered saturated, partially unsaturated, or aromatic bicyclic ring system containing 0–4 heteroatoms, said ring system optionally substituted with halo, R', —C(O)R' or C(O)OR'.

Z is N, CH, C(OCH₃), C(CH₃), C(NH₂), C(OH) or C(F).
W is CH, C(OCH₃), C(CH₃), C(NH₂), C(OH) or C(F).
J is T or is a (C₁–C₄) aliphatic substituted with T.
T is V, O(V) or NH(V).
V is C(O)N=C(R)(N(R)₂) wherein the two geminal R on the nitrogen are optionally taken together with the nitrogen to form a 4–8 membered heterocyclic ring.

Each R is independently selected from hydrogen, —R², —N(R²)₂, —OR², SR², —C(O)N(R²)₂, —S(O₂)N(R²)₂, —C(O)OR² or —C(O)R wherein two adjacent R are optionally bound to one another and, together with each C or N to which they are respectively bound, form a 4–8 membered carbocyclic or heterocyclic ring.

R² is selected from hydrogen; or a (C₁–C₃)-aliphatic optionally substituted with halo, —R', —N(R')₂, —OR', SR', —C(O)N(R')₂, —S(O₂)N(R')₂, —C(O)OR', —N(R')SO₂R⁸, —N(R')SO₂R⁷, —C(O)N(R')(R⁷), —N(R')C(O)R⁸, —N(R')(R⁷) —N(R')(R⁸), —C(O)R⁷, —C(O)N(R')(R⁸) —N(R⁸)₂, —C(O)N=C(NHR')₂ or R⁷.

R⁷ is selected from 5–8 membered aromatic or non-aromatic carbocyclic or heterocyclic ring systems each optionally substituted with halo, R', R⁸, —C(O)R', —C(O)R⁸, —C(O)OR⁸; or an 8–10 membered saturated, partially unsaturated, or aromatic bicyclic ring system containing 0–4 heteroatoms, said ring system optionally substituted with halo, R', R⁸, —C(O)R', —C(O)R⁸, or —C(O)OR⁸.

R⁸ is selected from C₂–C₄ aliphatic, wherein up to two saturated carbon atoms of the aliphatic chain are each optionally and independently replaced by —C(O)—, —C(O)NR'—, —C(O)NR'NR'—, —CO₂—, —NR'C(O)NR'—, —OC(O)—, —C(O)C(O)—, —OC(O)NR'—, —NR'NR'—, —NR'CO—, —NR'O—, —O—, —S—, —SO—, —SO₂—, —NR'—, —SO₂NR'—, —NR'SO₂—, and wherein the aliphatic chain is optionally substituted with halo, R', N(R')₂, OR', CO₂R', CON(R')₂, SO₂N(R')₂, SO₂N(R⁵)₂; a (C₁–C₇)-aliphatic optionally substituted with halo, R', N(R')₂, OR', CO₂R', CON(R')₂, SO₂N(R')₂, SO₂N(R⁵)₂; or a 5–6 membered carbocyclic or heterocyclic ring system optionally substituted with halo, R', N(R')₂, OR', CO₂R', C(O)N(R')₂, SO₂N(R')₂, or SO₂N(R⁵)₂.

K is —C(O)—D or a (C₁–C₄) aliphatic substituted with D or —OP(O)(OH)₂.

D is

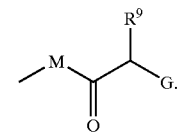

M is either O or NH.
G is selected from NH₂, OH, or H.
R⁹ is H; OH; C(O)OH; (C₁–C₇)-aliphatic optionally substituted with halo, R', N(R')₂, OR', CO₂R', CON(R')₂, or SO₂N(R')₂; or a 5–6 membered carbocyclic or heterocyclic ring system optionally substituted with halo, R', N(R')₂, OR', CO₂R', C(O)N(R')₂, or SO₂N(R')₂; or G and R⁹ taken together with the intervening carbon may form a ring. When G forms a ring with R⁹, it will be obvious to those skilled in the art that a terminal hydrogen from the unfused G and R⁹ component will be lost. For example, if a ring structure is formed by binding the G and R⁹ components together, one being —NH₂ and the other being —CH₂—CH₂—CH₂—

CH₃, one terminal hydrogen on each G or R⁹ component (indicated in bold) will be lost. Therefore, the resulting portion of the ring structure will have the formula —NH—CH₂—CH₂—CH₂—CH₂—.

Another embodiment of this invention is to provide methods of producing the above-identified inhibitors of p38.

In another embodiment, the invention provides pharmaceutical compositions comprising the p38 inhibitors of this invention. These compositions may be utilized in methods for treating or preventing a variety of disorders, such as cancer, inflammatory diseases autoimmune diseases, destructive bone disorders, proliferative disorders, infectious diseases, viral diseases and neurodegenerative diseases. These compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. Each of these above-described methods is also part of the present invention.

DETAILED DESCRIPTION OF THE INVENTION

These compounds have the general formulae:

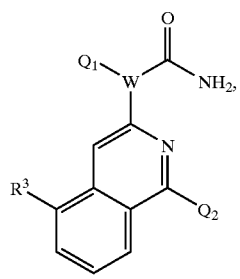

(Ia)

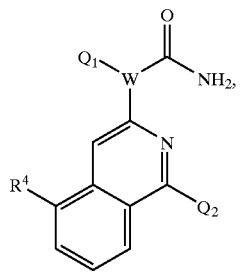

(Ib)

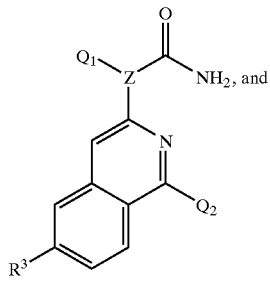

(Ic)

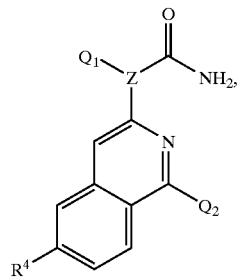

(Id)

wherein each of $Q_1$ and $Q_2$ are independently selected from a phenyl or 5–6 membered aromatic heterocyclic ring system, or an 8–14 membered saturated, partially unsaturated, or aromatic bicyclic or tricyclic ring system containing 0–4 heteroatoms.

The rings that make up $Q_1$ are substituted with 1 to 4 substituents, each of which is independently selected from halo; $C_1$–$C_3$ aliphatic optionally substituted with halo, R', N(R')₂, OR', CO₂R' or CON(R')₂; O—($C_1$–$C_3$)-aliphatic optionally substituted with halo, R', N(R')₂, OR', CO₂R' or CON(R')₂; R'; N(R')₂; OCF₃; CF₃; NO₂; CO₂R'; CON(R')₂; SR'; S(O₂)N(R')₂; SCF₃; CN; N(R')C(O)R⁴; N(R')C(O)OR⁴; N(R')C(O)C(O)R⁴; N(R')S(O₂)R⁴; N(R')R⁴; N(R⁴)₂; OR⁴; OC(O)R⁴; OP(O)₃H₂; N=CR'—N(R')₂; SO₂R'; or C(O)R'.

The rings that make up $Q_2$ are optionally substituted with up to 4 substituents, each of which is independently selected from halo; $C_1$–$C_3$ aliphatic optionally substituted with halo, R', N(R')₂, OR', CO₂R', S(O₂)N(R')₂, N=CR'—N(R')₂, R³, O—P(O₃)H₂, or CON(R')₂; O—($C_1$–$C_3$)-aliphatic optionally substituted with halo, R', N(R')₂, OR', CO₂R', S(O₂)N (R')₂, N=CR'—N(R')₂, R³, OP(O₃)H₂, or CON(R')₂; R'; N(R')₂; OCF₃; CF₃; NO₂; CO₂R'; CON(R')₂; R³; OR³; N(R³)₂; SR³; C(O)R³; C(O)N(R')R³; C(O)OR³; SR'; S(O₂)N(R')₂; SCF₃; N=CR'—N(R')₂; OR⁴; O—CO₂R⁴; N(R')C(O)R⁴; N(R')C(O)OR⁴; N(R')C(O)C(O)R⁴; N(R')S(O₂)R⁴; N(R')R⁴; N(R⁴)₂; OR⁴; OC(O)R⁴; OP(O)₃H₂; or CN.

Each R' is independently selected from hydrogen; ($C_1$–$C_3$)-aliphatic; phenyl or phenyl substituted with 1 to 3 substituents independently selected from halo, methoxy, cyano, nitro, amino, hydroxy, methyl or ethyl; or a 5–8 membered heterocyclic ring system optionally substituted with 1 to 3 substituents independently selected from halo, methoxy, cyano, nitro, amino, hydroxy, methyl or ethyl.

Each R³ is independently selected from a 5–8 membered aromatic or non-aromatic carbocyclic or heterocyclic ring systems each optionally substituted with halo, R', R⁴, —C(O)R', —C(O)R⁴, —C(O)R⁴, —J or —K; or an 8–10 membered saturated, partially unsaturated, or aromatic bicyclic ring system containing 0–4 heteroatoms, said ring system optionally substituted with halo, R', R⁴, —C(O)R', —C(O)R⁴, —C(O)OR⁴, —J or —K.

Each R⁴ is independently selected from —N(R')₂; —NR'C(O)—($C_1$–$C_4$)-aliphatic optionally substituted with halo, R', N(R')₂, OR', CO₂R', CON(R')₂, SO₂N(R')₂, SO₂N (R⁵)₂, —J or —K; —NR'—($C_1$–$C_4$)-aliphatic optionally substituted with halo, R', N(R')₂, OR', CO₂R', CON(R')₂, SO₂N(R')₂, SO₂N(R⁵)₂, —J or —K; —OC(O)—N(R')₂; a $C_1$–$C_4$ aliphatic, wherein up to two saturated carbon atoms of the aliphatic chain are each optionally and independently replaced by —C(O)—, —C(O)NR'—, —C(O)NR'NR'—, —CO₂—, —NR'C(O)NR'—, —OC(O)—, —C(O)C(O)—, —OC(O)NR'—, —NR'NR'—, —NR'CO—, —NR'O—, —O—, —S—, —SO—, —SO$_2$—, —NR'—, —SO$_2$NR'—, —NR'SO$_2$—, and wherein the aliphatic chain is optionally substituted with halo, R', N(R')$_2$, OR', CO$_2$R', CON(R')$_2$, SO$_2$N(R')$_2$, SO$_2$N(R$^5$)$_2$, —J or —K; a (C$_1$-C$_7$)-aliphatic optionally substituted with halo, R', N(R')$_2$, OR', CO$_2$R', CON(R')$_2$, SO$_2$N(R')$_2$, SO$_2$N(R$^5$)$_2$, —J or —K; —J; —K; or a 5–6 membered aromatic or non-aromatic carbocyclic or heterocyclic ring system optionally substituted with halo, R', N(R')$_2$, OR', CO$_2$R', C(O)N(R')$_2$, SO$_2$N(R')$_2$SO$_2$N(R$^5$)$_2$, —J or —K.

R$^5$ is selected from hydrogen; or a (C$_1$-C$_3$)-aliphatic optionally substituted with halo, —R', —N(R')$_2$, —OR', SR', —C(O)N(R')$_2$, —S(O)$_2$N(R')$_2$, —C(O)OR'—N(R')S(O)$_2$(R')—N(R')SO$_2$R$^6$, —C(O)N(R')(R$^6$), —N(R')C(O)R', —N(R')(R$^6$), —C(O)R$^6$, —C(O)N═C(NHR')$_2$ or R$^6$.

R$^6$ is selected from 5–8 membered aromatic or non-aromatic carbocyclic or heterocyclic ring systems each optionally substituted with halo, R', —C(O)R' or —C(O)OR'; or an 8–10 membered saturated, partially unsaturated, or aromatic bicyclic ring system containing 0–4 heteroatoms, said ring system optionally substituted with halo, R', —C(O)R' or C(O)OR'.

Z is N, CH, C(OCH$_3$), C(CH$_3$), C(NH$_2$), C(OH) or C(F).

W is CH, C(OCH$_3$), C(CH$_3$), C(NH$_2$), C(OH) or C(F).

J is T or is a (C$_1$-C$_4$) aliphatic substituted with T.

T is V, O(V), or NH(V).

V is C(O)N═C(R)(N(R)$_2$) wherein the two geminal R on the nitrogen are optionally taken together with the nitrogen to form a 4–8 membered heterocyclic ring.

Each R is independently selected from hydrogen, —R$^2$, —N(R$^2$)$_2$, —OR$^2$, SR$^2$, —C(O)N(R$^2$)$_2$, —S(O$_2$)N(R$^2$)$_2$, —C(O)OR$^2$ or —C(O)R$^2$ wherein two adjacent R are optionally bound to one another and, together with each C or N to which they are respectively bound, form a 4–8 membered carbocyclic or heterocyclic ring.

R$^2$ is selected from hydrogen; or a (C$_1$-C$_3$)-aliphatic optionally substituted with halo, —R', —N(R')$_2$, —OR', SR', —C(O)N(R')$_2$, —S(O$_2$)N(R')$_2$, —C(O)OR', —N(R')SO$_2$R$^8$, —N(R')SO$_2$R$^7$, —C(O)N(R')(R$^7$), —N(R')C(O)R$^8$, —N(R')(R$^7$)—N(R')(R$^8$), —C(O)R$^7$, —C(O)N(R')(R$^8$), —N(R$^8$)$_2$, —C(O)N═C(NHR')$_2$ or R$^7$.

R$^7$ is selected from 5–8 membered aromatic or non-aromatic carbocyclic or heterocyclic ring systems each optionally substituted with halo, R', R$^8$, —C(O)R', —C(O)R$^8$, —C(O)OR$^8$; or an 8–10 membered saturated, partially unsaturated, or aromatic bicyclic ring system containing 0–4 heteroatoms, said ring system optionally substituted with halo, R', R$^8$, —C(O)R', —C(O)R$^8$, or —C(O)OR$^8$.

R$^8$ is selected from C$_1$-C$_4$ aliphatic, wherein up to two saturated carbon atoms of the aliphatic chain are each optionally and independently replaced by —C(O)—, —C(O)NR'—, —C(O)NR'NR'—, —CO$_2$—, —NR'C(O)NR'—, —OC(O)—, —C(O)C(O)—, —OC(O)NR'—, —NR'NR'—, —NR'CO—, —NR'O—, —O—, —S—, —SO—, —SO$_2$—, —NR'—, —SO$_2$NR'—, —NR'SO$_2$—, and wherein the aliphatic chain is optionally substituted with halo, R', N(R')$_2$, OR', CO$_2$R', CON(R')$_2$, SO$_2$N(R')$_2$, SO$_2$N(R$^5$)$_2$; a (C$_1$-C$_7$)-aliphatic optionally substituted with halo, R', N(R')$_2$, OR', CO$_2$R', CON(R')$_2$, SO$_2$N(R')$_2$, SO$_2$N(R$^5$)$_2$; or a 5–6 membered carbocyclic or heterocyclic ring system optionally substituted with halo, R', N(R')$_2$, OR', CO$_2$R', C(O)N(R')$_2$, SO$_2$N(R')$_2$, or SO$_2$N(R$^5$)$_2$.

K is —C(O)—D or a (C$_1$-C$_4$) aliphatic substituted with —D or —OP(O)(OH)$_2$.

D is

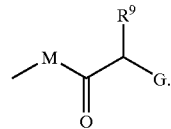

M is either O or NH.

G is selected from NH$_2$, OH, or H.

R$^9$ is H; OH; C(O)OH; (C$_1$-C$_7$)-aliphatic optionally substituted with halo, R', N(R')$_2$, OR', CO$_2$R', CON(R')$_2$, or SO$_2$N(R')$_2$; or a 5–6 membered carbocyclic or heterocyclic ring system optionally substituted with halo, R', N(R')$_2$, OR', CO$_2$R', C(O)N(R')$_2$, or SO$_2$N(R')$_2$; or G and R$^9$ taken together with the intervening carbon may form a ring. When G forms a ring with R$^9$, it will be obvious to those skilled in the art that a terminal hydrogen from the unfused G and R$^9$ component will be lost. For example, if a ring structure is formed by binding the G and R$^9$ components together, one being —NH$_2$ and the other being —CH$_2$—CH$_2$—CH$_2$—CH$_3$, one terminal hydrogen on each G or R$^9$ component (indicated in bold) will be lost. Therefore, the resulting portion of the ring structure will have the formula —NH—CH$_2$—CH$_2$—CH$_2$—CH$_2$—.

As used herein, the following definitions shall apply unless otherwise indicated. Also, combinations of substituents or variables are permissible only if such combinations result in stable compounds.

The term "aliphatic" as used herein means straight-chain, branched or cyclic C$_1$-C$_{12}$ hydrocarbons which are completely saturated or which contain one or more units of unsaturation. For example, suitable aliphatic groups include substituted or unsubstituted linear, branched or cyclic alkyl, alkenyl, alkynyl groups and hybrids thereof such as (cycloalkyl)alkyl, (cycloalkenyl) alkyl or (cycloalkyl) alkenyl. The term "alkyl" used alone or as part of a larger moiety refers to both straight and branched chains containing one to twelve carbon atoms. The terms "alkenyl" and "alkynyl" used alone or as part of a larger moiety shall include both straight and branched chains containing two to twelve carbon atoms. The terms "haloalkyl", "haloalkenyl" and "haloalkoxy" means alkyl, alkenyl or alkoxy, as the case may be, substituted with one or more halogen atoms. The term "halogen" means F, Cl, Br, or I. The term "heteroatom" means N, O, or S and shall include any oxidized form of nitrogen and sulfur, and the quaternized form of any basic nitrogen.

A heterocyclic ring system or a heterocyclic ring contains 1 to 4 heteroatoms, which are independently selected from N, O, and S. A substitutable nitrogen on an aromatic or non-aromatic heterocyclic ring may be optionally substituted. N or S may also exist in oxidized form such as NO, SO and SO$_2$.

One having ordinary skill in the art will recognize that the maximum number of heteroatoms in a stable, chemically feasible heterocyclic ring, whether it is aromatic or non-aromatic, is determined by the size of the ring, degree of unsaturation, and valence of the heteroatoms. In general, a heterocyclic ring may have one to four heteroatoms so long as the heterocyclic ring is chemically feasible and stable.

The term "chemically stable arrangement" or "chemically feasible and stable" as used herein, refers to a compound structure that renders the compound sufficiently stable to allow manufacture and administration to a mammal by methods known in the art. Typically, such compounds are stable at a temperature of 40° C. or less, in the absence of moisture or other chemically reactive conditions, for at least a week.

Carbocyclic and heterocyclic aromatic ring systems have five to fourteen members, and include, without limitation, phenyl, benzyl, 1-naphthyl, 2-naphthyl, 1-anthracyl and 2-anthracyl, and heterocyclic aromatic ring systems such as 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, or 3-thienyl. The term "aromatic ring system" also refers to rings that are optionally substituted.

Aromatic ring systems may also include fused polycyclic aromatic ring systems in which a carbocyclic aromatic ring or heterocyclic aromatic ring is fused to one or more other rings. Examples include tetrahydronaphthyl, benzimidazolyl, benzothienyl, benzofuranyl, indolyl, quinolinyl, benzothiazolyl, benzooxazolyl, benzimidazolyl, isoquinolinyl, isoindolyl, acridinyl, benzoisoxazolyl, and the like. Aromatic ring systems also include groups in which one or more carbocyclic aromatic rings and/or heteroaryl rings are fused to a cycloalkyl or non-aromatic heterocyclic ring, for example, indanyl or tetrahydrobenzopyranyl.

Non-aromatic heterocyclic rings are non-aromatic carbocyclic rings in which one or more ring carbons are replaced by a heteroatom such as nitrogen, oxygen or sulfur in the ring. The ring can be five, six, seven or eight-membered and/or fused to another ring, such as a cycloalkyl or aromatic ring. Examples include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, and benzothiane. The term "heterocyclic ring", whether saturated or unsaturated, also refers to rings that are optionally substituted.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

According to a preferred embodiment, $Q_1$ is selected from phenyl or pyridyl containing 1 to 3 substituents, wherein at least one of said substituents is in the ortho position and said substituents are independently selected from chloro, fluoro, bromo, —$CH_3$, —$OCH_3$, —OH, —$CF_3$, —$OCF_3$, —$O(CH_2)_2CH_3$, $NH_2$, 3,4-methylenedioxy, —$N(CH_3)_2$, —NH—$S(O)_2$-phenyl, —NH—C(O)O—$CH_2$-4-pyridine, —NH—C(O)$CH_2$-morpholine, —NH—C(O)$CH_2$—N$(CH_3)_2$, —NH—C(O)$CH_2$-piperazine, —NH—C(O)$CH_2$-pyrrolidine, —NH—C(O)C(O)-morpholine, —NH—C(O)C(O)-piperazine, —NH—C(O)C(O)-pyrrolidine, —O—C(O)$CH_2$—N$(CH_3)_2$, or —O—$(CH_2)_2$—N$(CH_3)_2$.

Even more preferred are phenyl or pyridyl containing at least 2 of the above-indicated substituents both being in the ortho position.

Some specific examples of preferred $Q_1$ are:

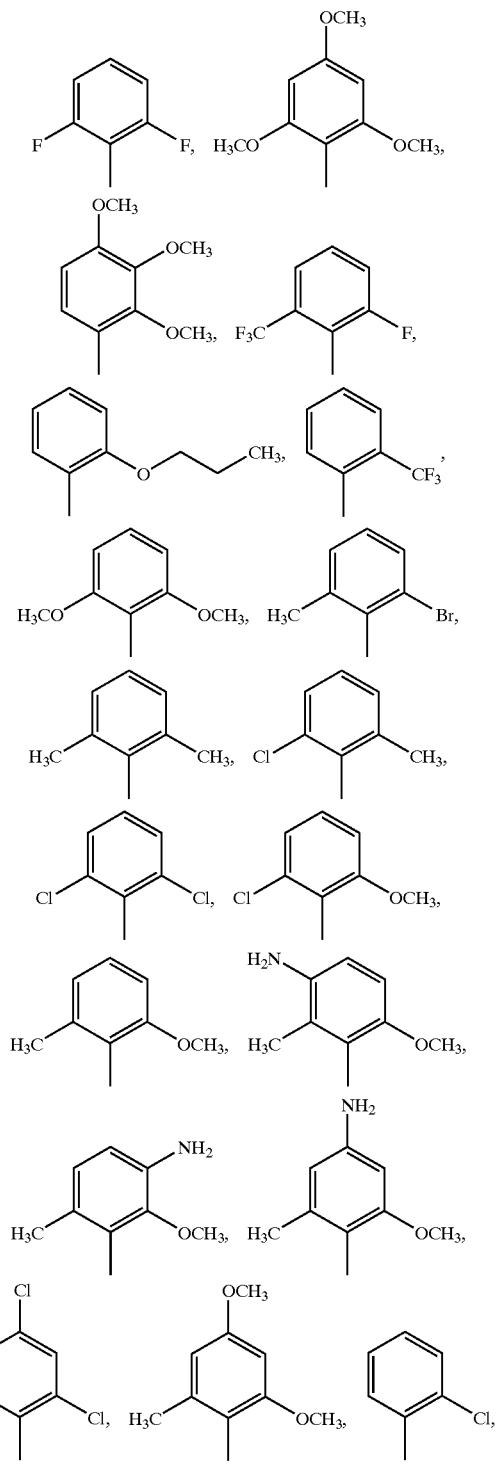

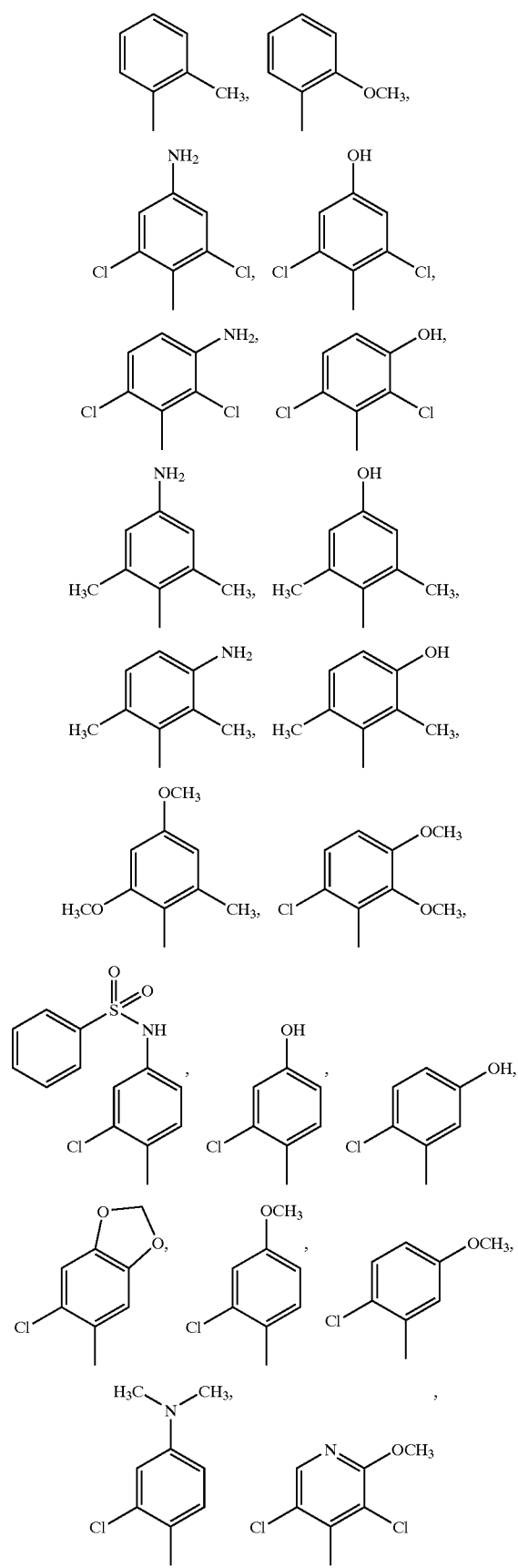
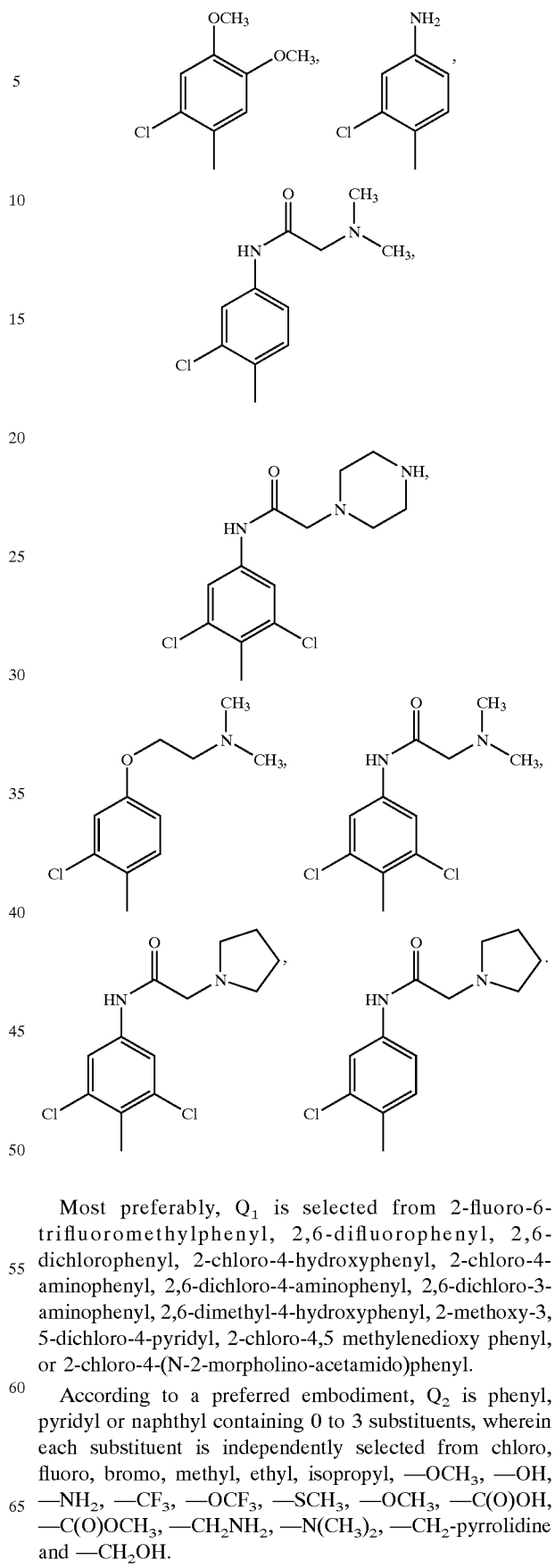

Most preferably, $Q_1$ is selected from 2-fluoro-6-trifluoromethylphenyl, 2,6-difluorophenyl, 2,6-dichlorophenyl, 2-chloro-4-hydroxyphenyl, 2-chloro-4-aminophenyl, 2,6-dichloro-4-aminophenyl, 2,6-dichloro-3-aminophenyl, 2,6-dimethyl-4-hydroxyphenyl, 2-methoxy-3,5-dichloro-4-pyridyl, 2-chloro-4,5 methylenedioxy phenyl, or 2-chloro-4-(N-2-morpholino-acetamido)phenyl.

According to a preferred embodiment, $Q_2$ is phenyl, pyridyl or naphthyl containing 0 to 3 substituents, wherein each substituent is independently selected from chloro, fluoro, bromo, methyl, ethyl, isopropyl, —$OCH_3$, —OH, —$NH_2$, —$CF_3$, —$OCF_3$, —$SCH_3$, —$OCH_3$, —C(O)OH, —C(O)$OCH_3$, —$CH_2NH_2$, —N($CH_3$)$_2$, —$CH_2$-pyrrolidine and —$CH_2OH$.

Some specific examples of preferred $Q_2$ are:
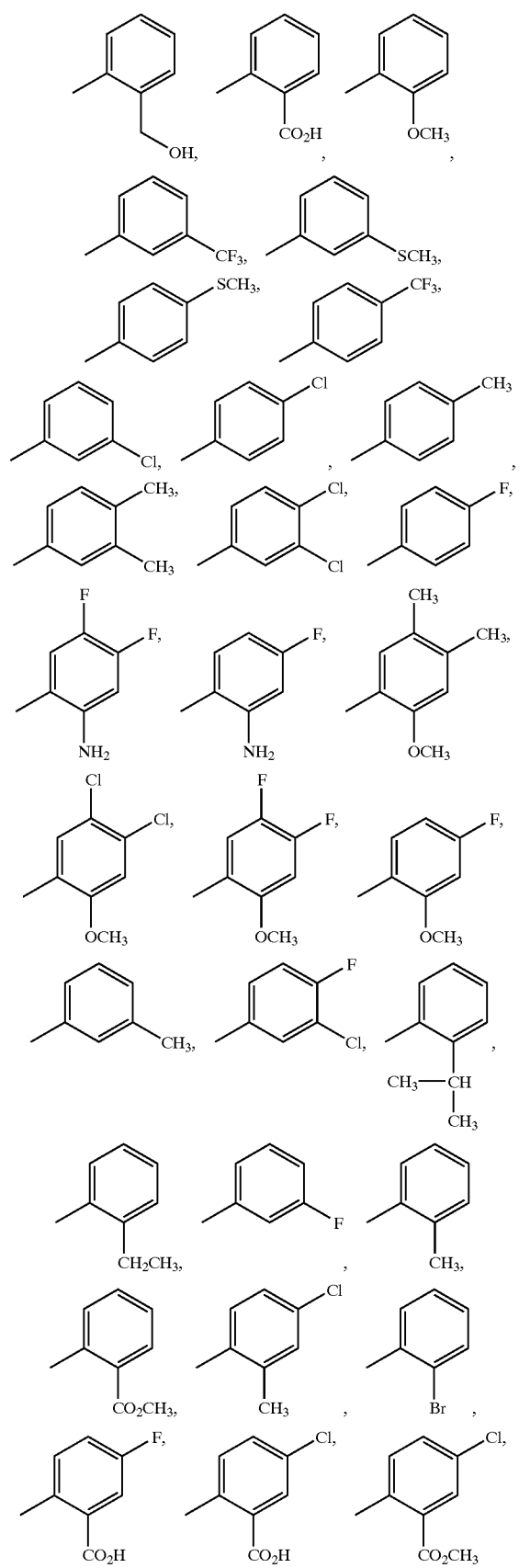
-continued
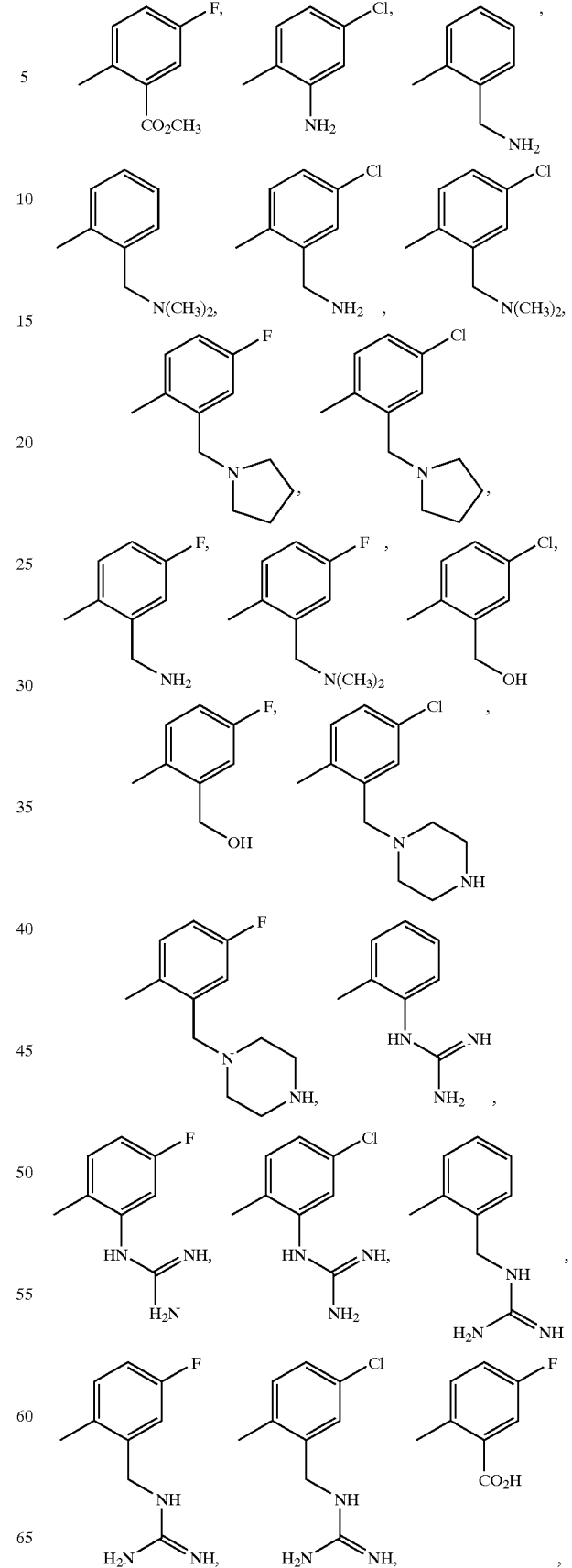

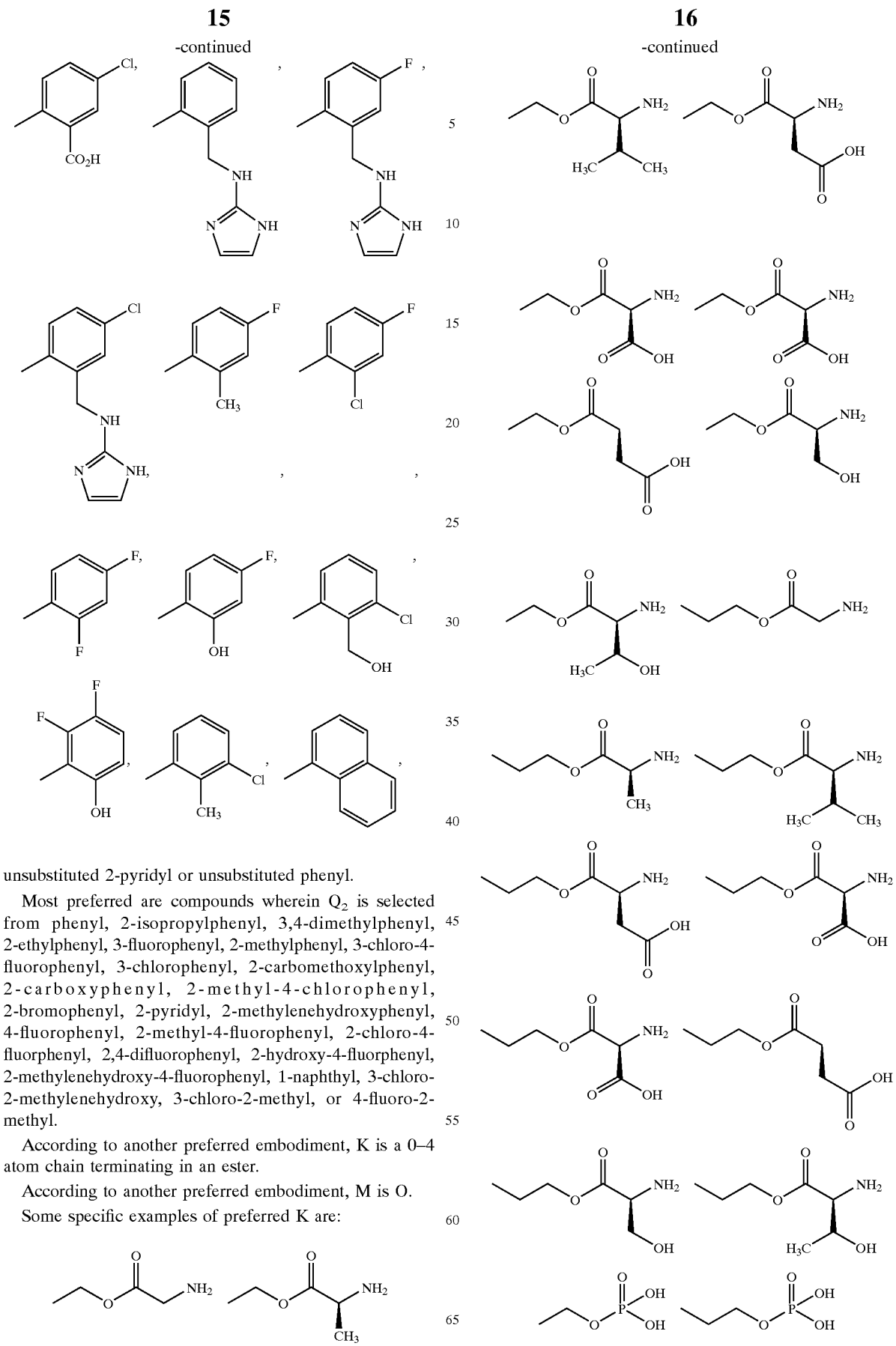

unsubstituted 2-pyridyl or unsubstituted phenyl.

Most preferred are compounds wherein $Q_2$ is selected from phenyl, 2-isopropylphenyl, 3,4-dimethylphenyl, 2-ethylphenyl, 3-fluorophenyl, 2-methylphenyl, 3-chloro-4-fluorophenyl, 3-chlorophenyl, 2-carbomethoxyphenyl, 2-carboxyphenyl, 2-methyl-4-chlorophenyl, 2-bromophenyl, 2-pyridyl, 2-methylenehydroxyphenyl, 4-fluorophenyl, 2-methyl-4-fluorophenyl, 2-chloro-4-fluorphenyl, 2,4-difluorophenyl, 2-hydroxy-4-fluorphenyl, 2-methylenehydroxy-4-fluorophenyl, 1-naphthyl, 3-chloro-2-methylenehydroxy, 3-chloro-2-methyl, or 4-fluoro-2-methyl.

According to another preferred embodiment, K is a 0–4 atom chain terminating in an ester.

According to another preferred embodiment, M is O.

Some specific examples of preferred K are:

-continued
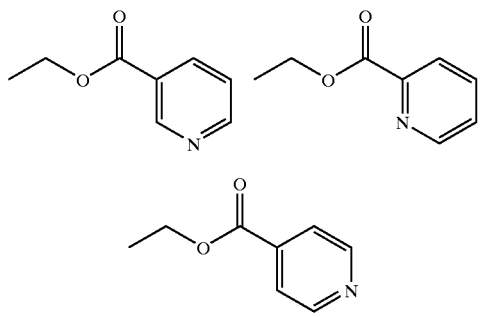
Most preferably, K is selected from:
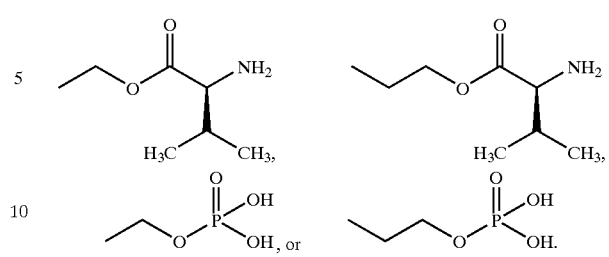
In another preferred embodiment, Z is N and W is CH. Some preferred embodiments are provided in Tables 1 and 2 below:
TABLE 1
| Cmpd Nmbr | Structure | Cmpd Nmbr | Structure |
|---|---|---|---|
| 101 | 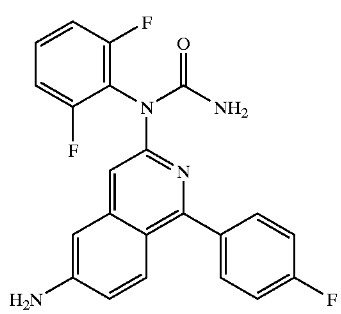 | 102 | 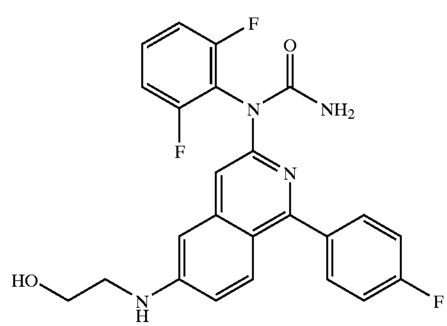 |
| 103 | 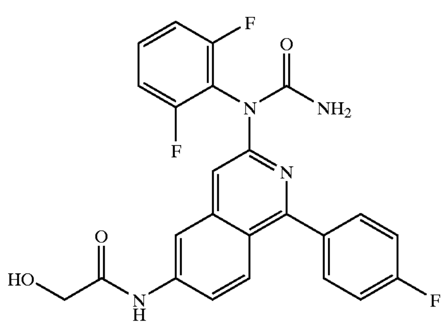 | 104 | 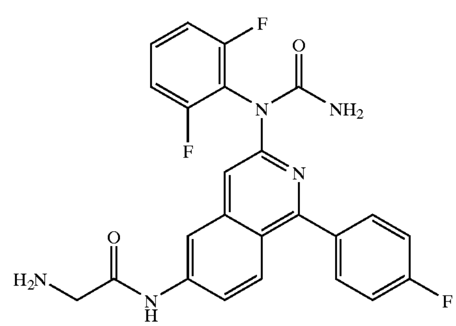 |
| 105 | 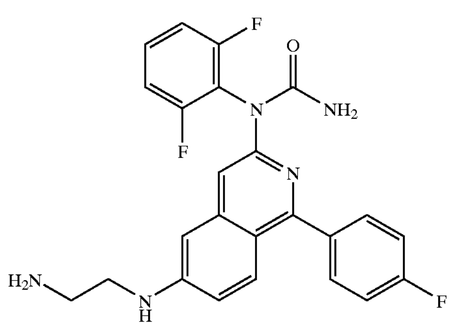 | 106 | 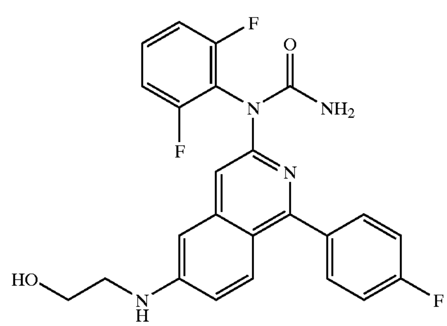 |

TABLE 1-continued

| Cmpd Nmbr | Structure | Cmpd Nmbr | Structure |
|---|---|---|---|
| 107 | 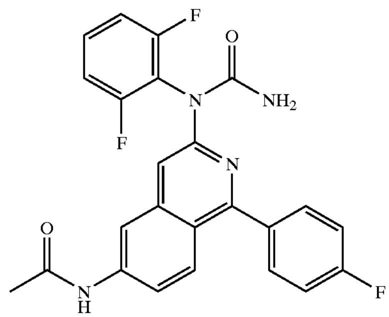 | 108 | 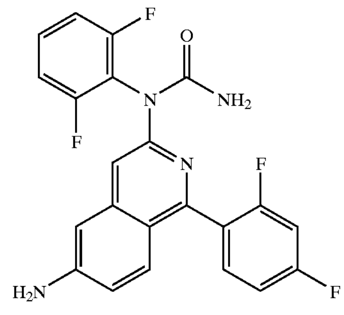 |
| 109 | 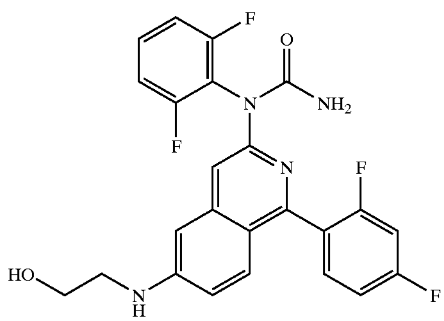 | 110 | 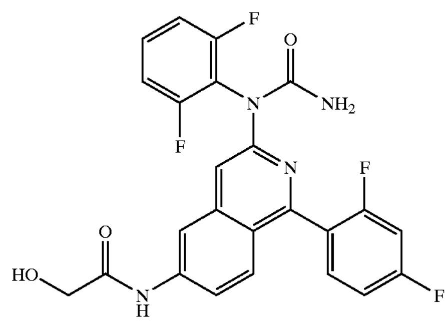 |
| 111 | 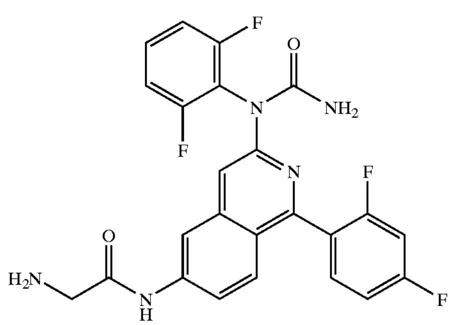 | 112 | 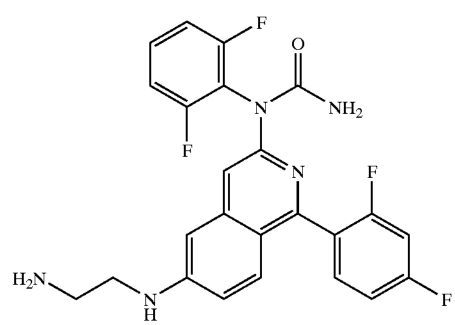 |
| 113 | 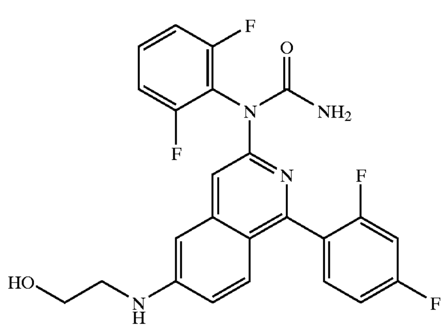 | 114 | 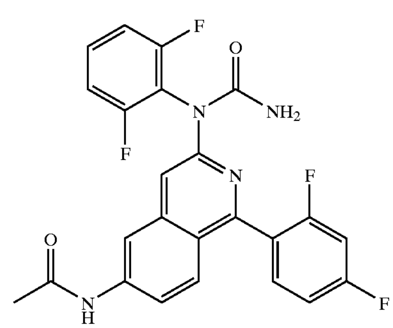 |

TABLE 2

| Cmpd Nmbr | Structure | Cmpd Nmbr | Structure |
|---|---|---|---|
| 201 | 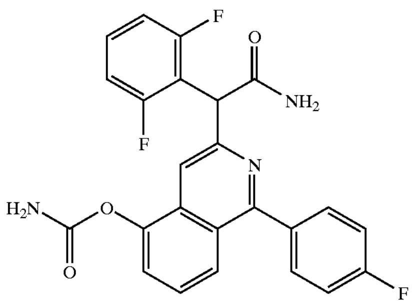 | 202 | 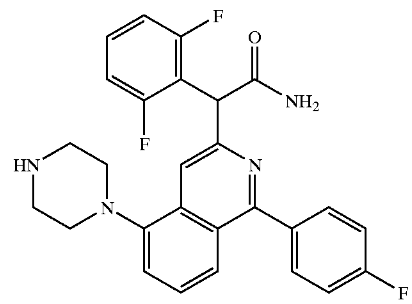 |
| 203 | 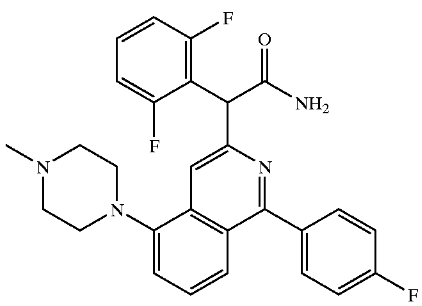 | 204 | 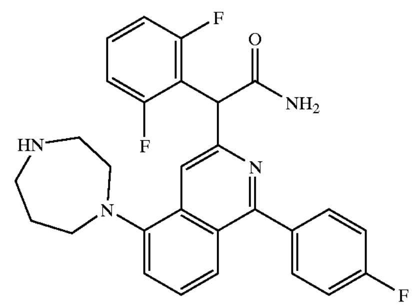 |
| 205 | 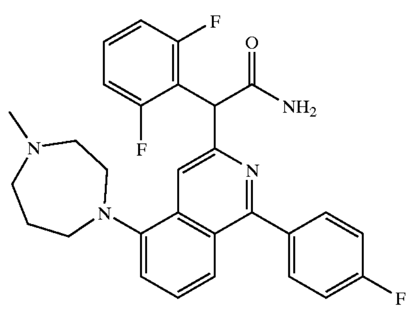 | 206 | 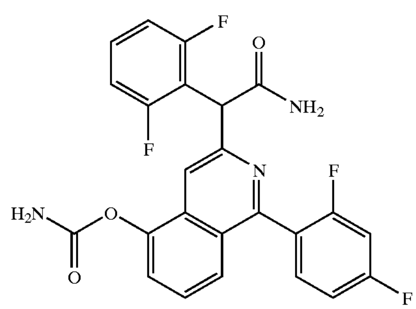 |
| 207 | 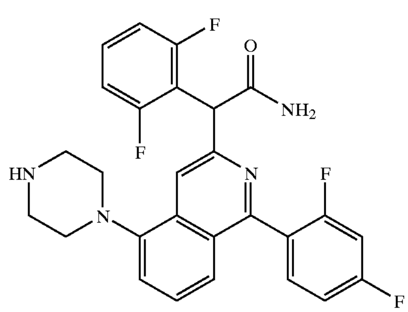 | 208 | 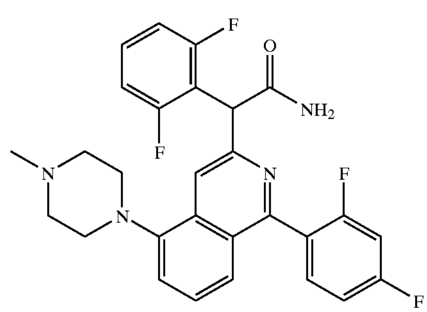 |
| 209 | 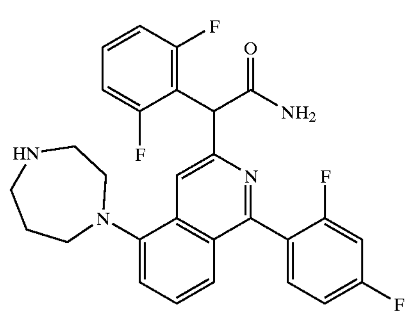 | 210 | 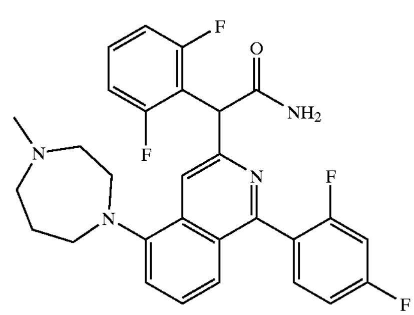 |

TABLE 2-continued
| Cmpd Nmbr | Structure | Cmpd Nmbr | Structure |
|---|---|---|---|
| 211 | 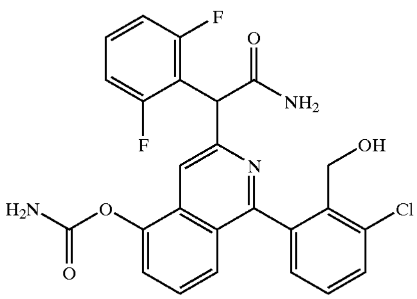 | 212 | 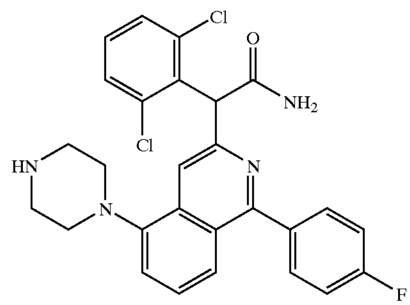 |
| 213 | 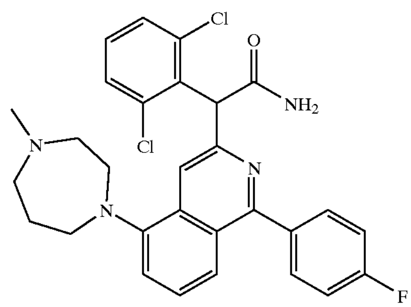 | 214 | 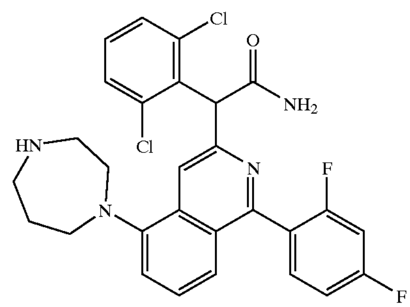 |
| 215 | 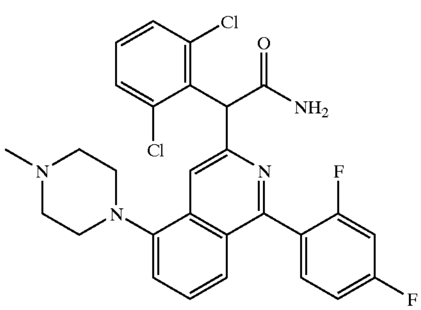 | | |
Particularly preferred embodiments include:
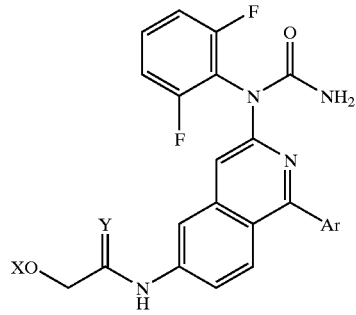
wherein Ar is
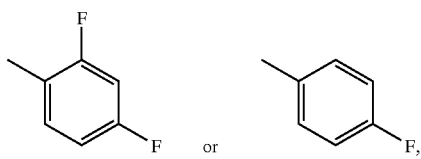
Y is $H_2$ or O, and X=

Particularly preferred embodiments also include:
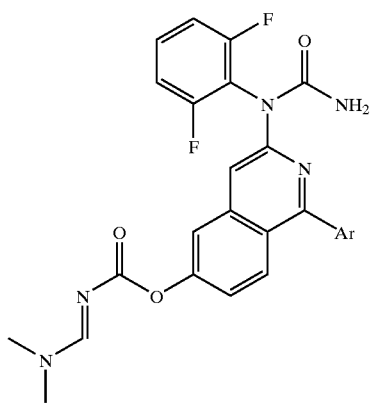
wherein Ar is
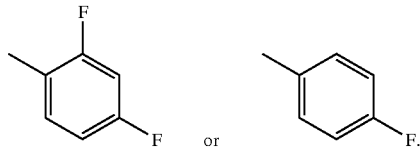
Other particularly preferred embodiments include:
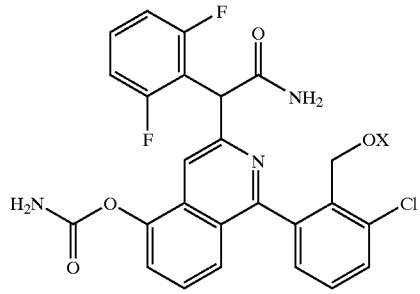
wherein X=
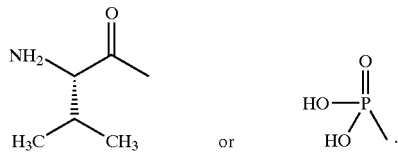
Other particularly preferred embodiments include:
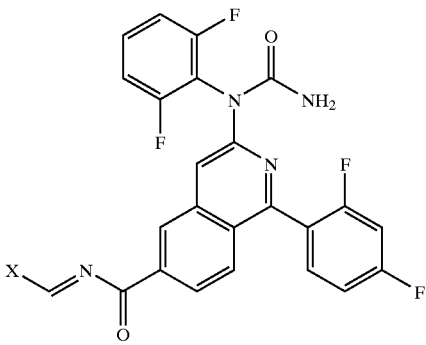
wherein X is $N(CH_3)_2$,
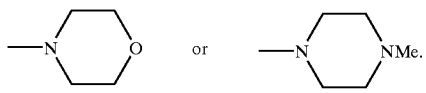
Other particularly preferred embodiments include:
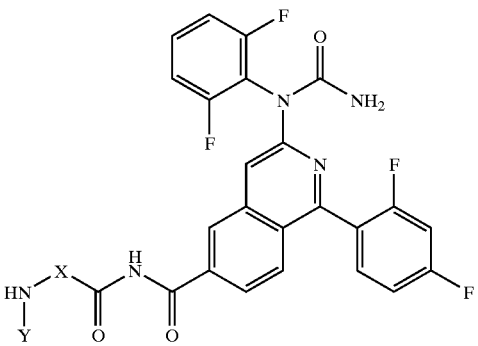
wherein Y=Me or H; and X=$(CH_2)_3$, $CH_2C(CH_3)_2CH_2$, $CH_2N(Me)C(O)CH_2$.
Most preferred embodiments include:
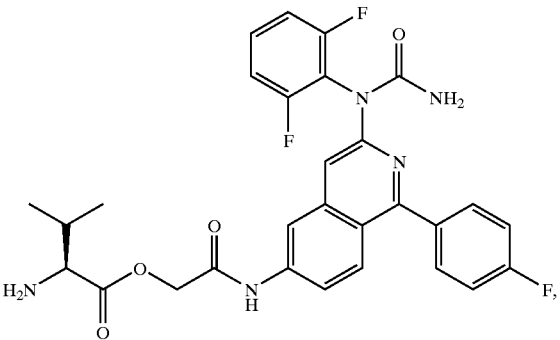

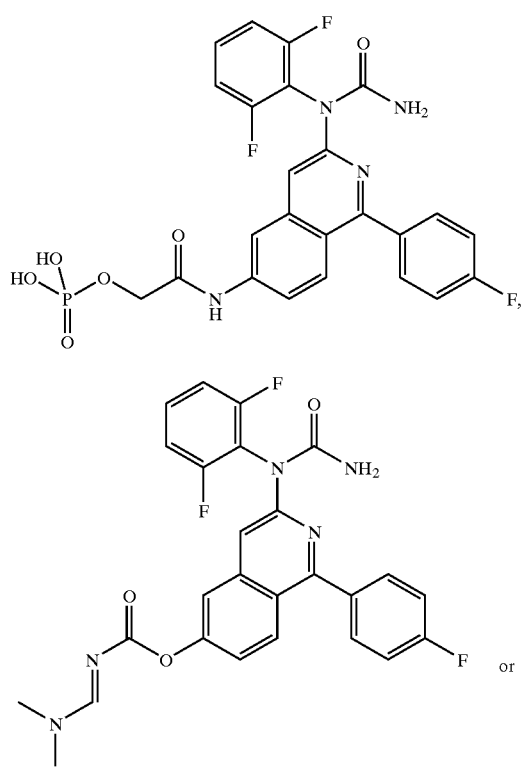
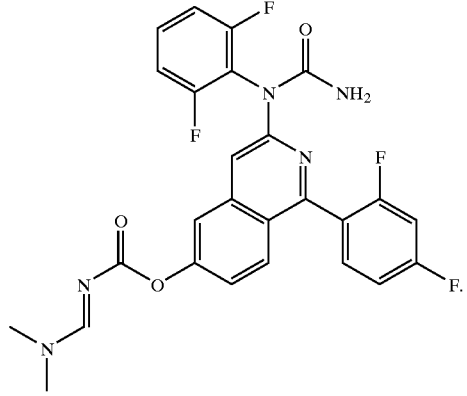 or
According to another embodiment, the present invention provides methods of producing the above-identified inhibitors of p38 of the formulae (Ia), (Ib), (Ic), and (Id). Representative synthetic schemes are depicted below.
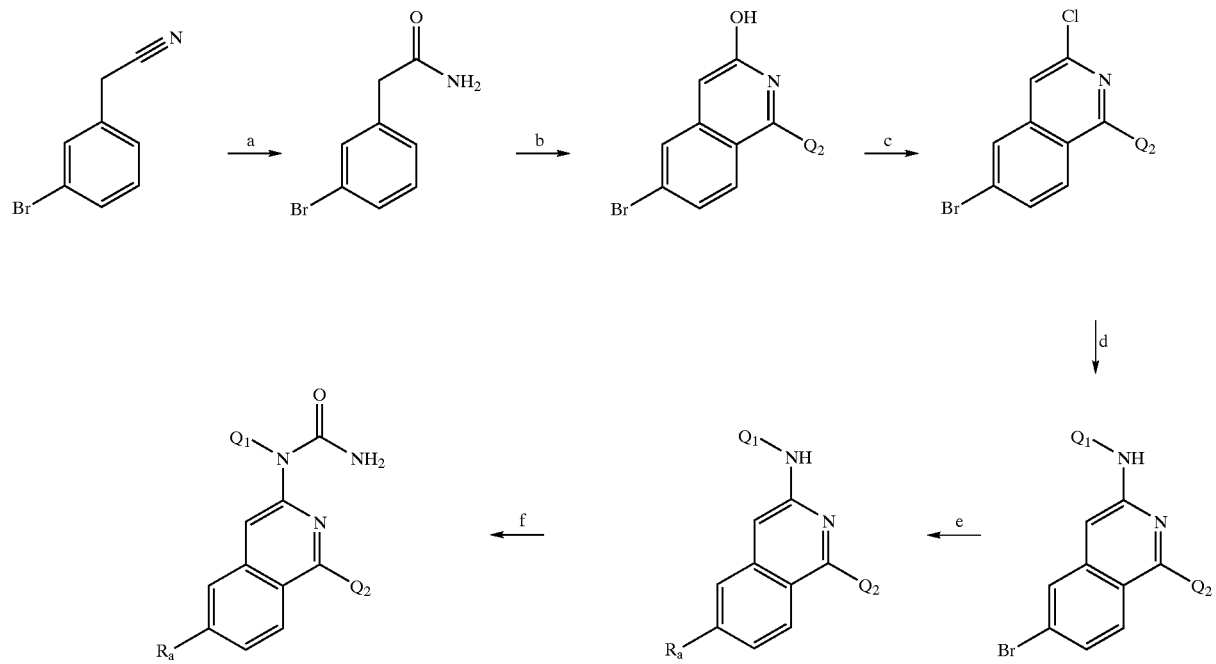
Conditions:
a) conc. H$_2$SO$_4$;
b) Q$_2$CHO, pTsOH, toluene;
c) POCl$_3$;
d) Q$_1$NH$_2$, NaH, THF;
e) R$_a$B(OH)$_2$, CsF, DME, Pd(PPh$_3$)$_4$;
f) i. ClO(O)Cl, ii) NH$_2$OH.

Scheme 1 may be used to synthesize compounds having the general formula of (Ic) or (Id) wherein Z=N and $R^3$ or $R^4$=$R_a$. Scheme 1 may be used to synthesize carbon-linked $R^3$ or $R^4$ substituents.

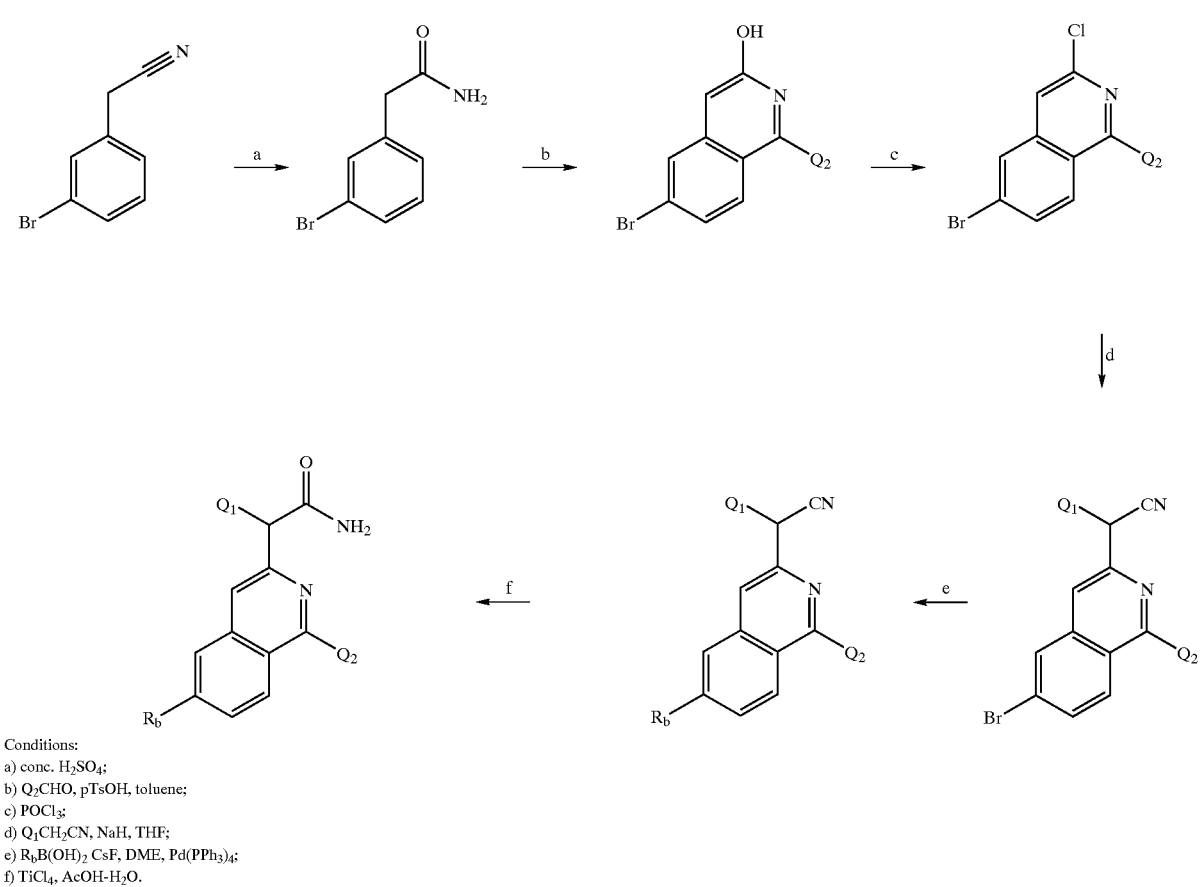

Conditions:
a) conc. $H_2SO_4$;
b) $Q_2CHO$, pTsOH, toluene;
c) $POCl_3$;
d) $Q_1CH_2CN$, NaH, THF;
e) $R_bB(OH)_2$ CsF, DME, $Pd(PPh_3)_4$;
f) $TiCl_4$, AcOH-$H_2O$.

Scheme 2 may be used to synthesize compounds having the general formula of (Ic) or (Id) wherein Z=CH and $R^3$ or $R^4$=$R_b$. Scheme 2 may be used to synthesize carbon-linked $R^3$ or $R^4$ substituents.

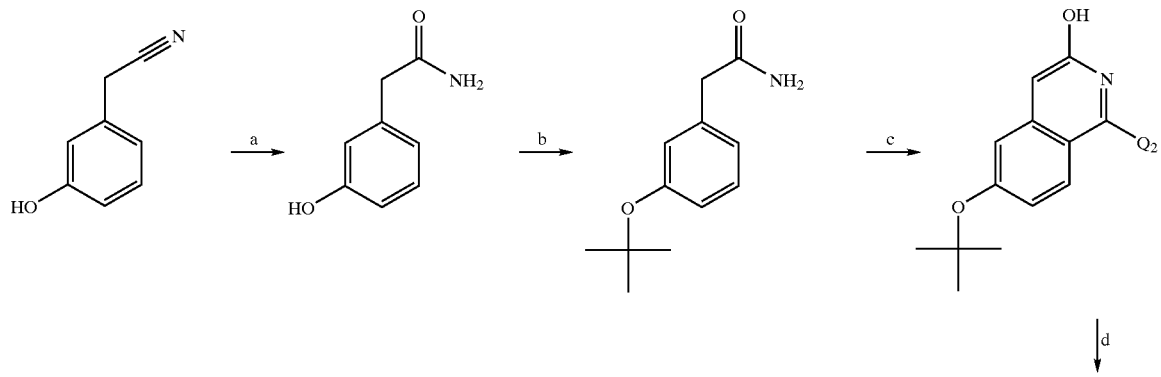

-continued

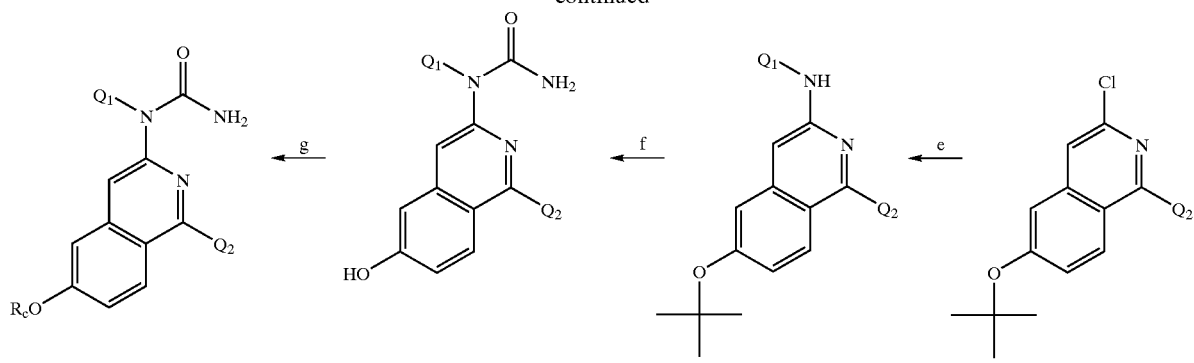

Conditions:
a) conc. H$_2$SO$_4$;
b) isobutylene, Amberlyst-15;
c) Q$_2$CHO; pTsOH, toluene;
d) POCl$_3$;
e) Q$_1$NH$_2$, NaH, THF;
f) i. ClC(O)Cl, ii) NH$_2$OH;
g) R$_c$Br, K$_2$CO$_3$, THF.

Scheme 3 may be used to synthesize compounds having the general formula of (Ic) or (Id) wherein Z=N and R$^3$ or R$^4$=OR$_c$. Scheme 3 may be used to synthesize O-linked R$^3$ and R$^4$ substituents.

Scheme 4 may be used to synthesize compounds having the general formula of (Ic) or (Id) wherein Z=CH and R$^3$ or R$^4$=OR. Scheme 4 may be used to synthesize O-linked R$^3$ and R$^4$ substituents.

Scheme 4

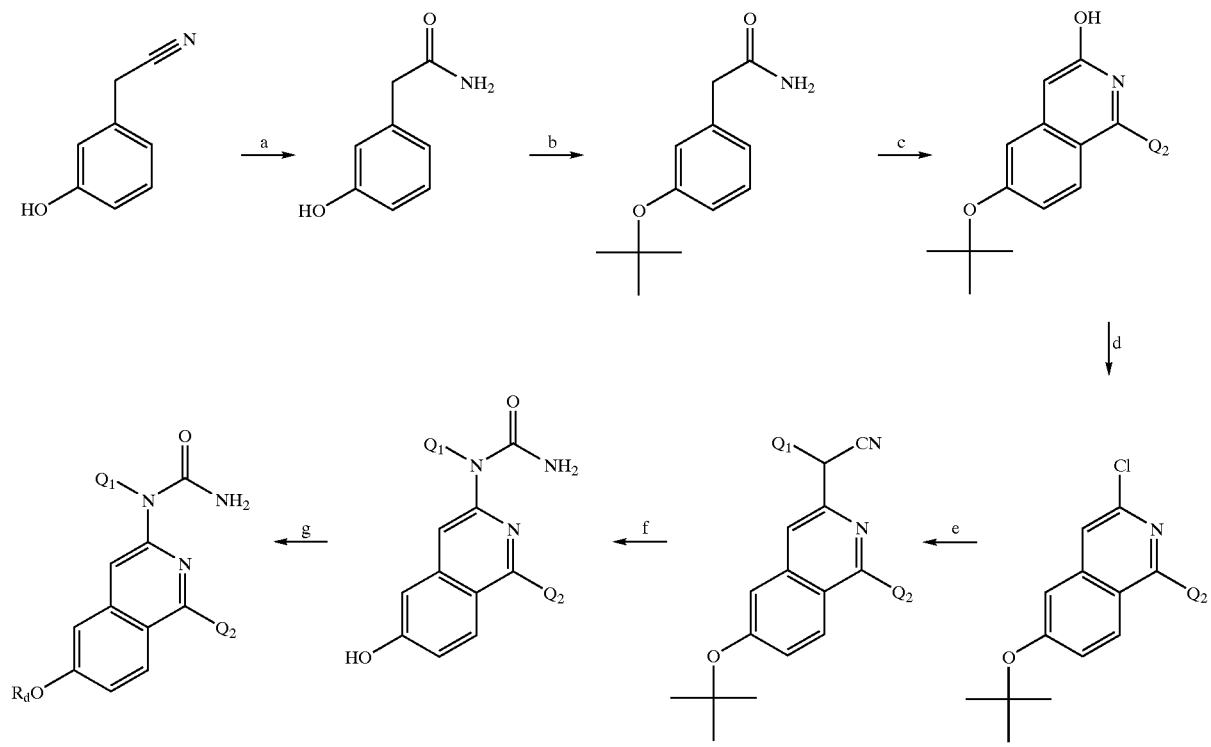

Conditions:
a) aq. H$_2$SO$_4$;
b) isobutylene, Amberlyst-15;
c) Q$_2$CHO, pTsOH, toluene;
d) POCl$_3$;
e) Q$_1$CH$_2$CN, NaH, THF;
f) TiCl$_4$, AcOH-H$_2$O
g) K$_2$CO$_3$, THF.

Scheme 5

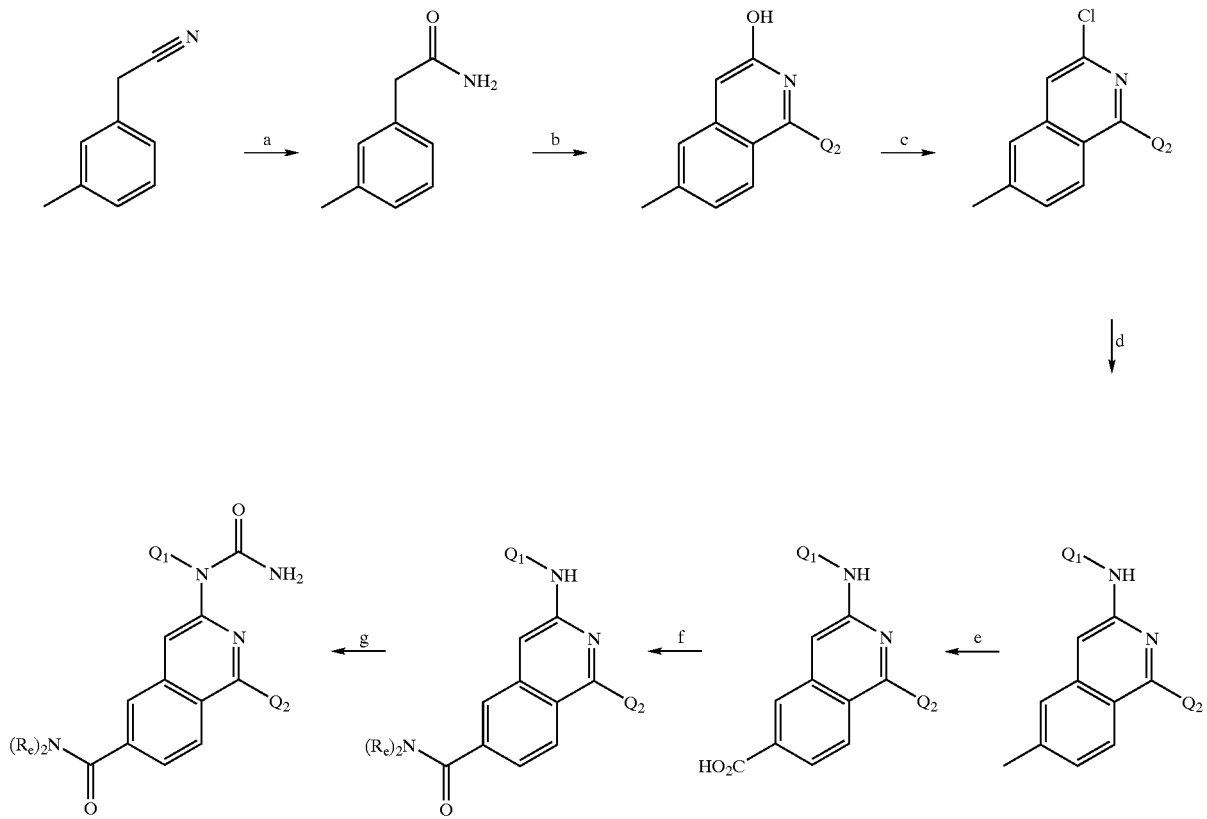

Conditions:
a) conc. $H_2SO_4$;
b) $Q_2CHO$, pTsOH, toluene;
c) $POCl_3$;
d) $Q_1NH_2$, NaH, THF;
e) $KMnO_4$;
f) i. ClC(O)C(O)Cl, ii) $HN(R_e)_2$;
g) ClC(O)Cl, ii) $NH_4OH$.

Scheme 5 may be used to synthesize compounds having the general formula of (Ic) or (Id) wherein Z=N and $R^3$ or $R^4$=C(O)N($R_e$)$_2$. One having skill in the art will recognize that unsymmetrical amine derivatives may also be used. Scheme 5 may be used to synthesize C(O)—N-linked $R^3$ and $R^4$ substituents.

Scheme 6

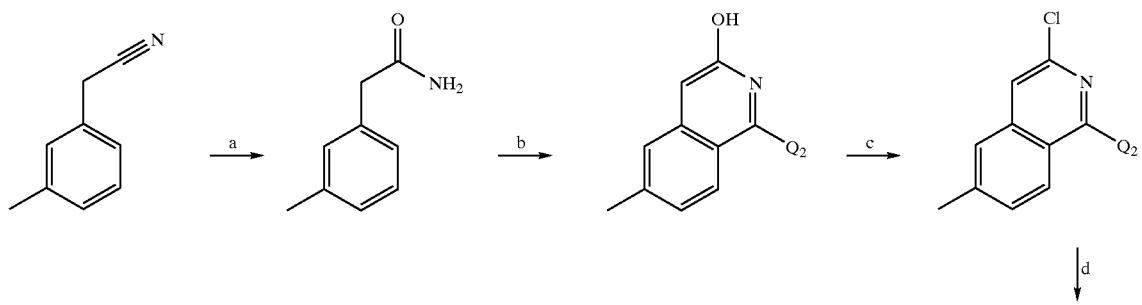

-continued

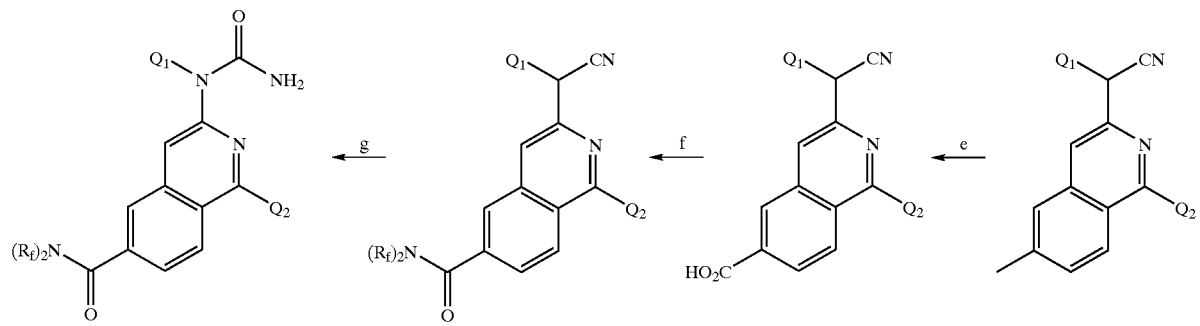

Conditions:
a) conc. H$_2$SO$_4$;
b) Q$_2$CHO, pTsOH, toluene;
c) POCl$_3$;
d) Q$_1$CH$_2$CN, NaH, THF;
e) KMnO$_4$;
f) i. ClC(O)C(O)Cl, ii. HN(R$_f$)$_2$;
g) TiCl$_4$, AcOH-H$_2$O.

Scheme 6 may be used to synthesize compounds having the general formula of (Ic) or (Id) wherein Z=CH and R$^3$ or R$^4$=C(O)N(R$_f$)$_2$. One having skill in the art will recognize that unsymmetrical amine derivatives may also be used. Scheme 6 may be used to synthesize C(O)N-linked R$^3$ and R$^4$ substituents.

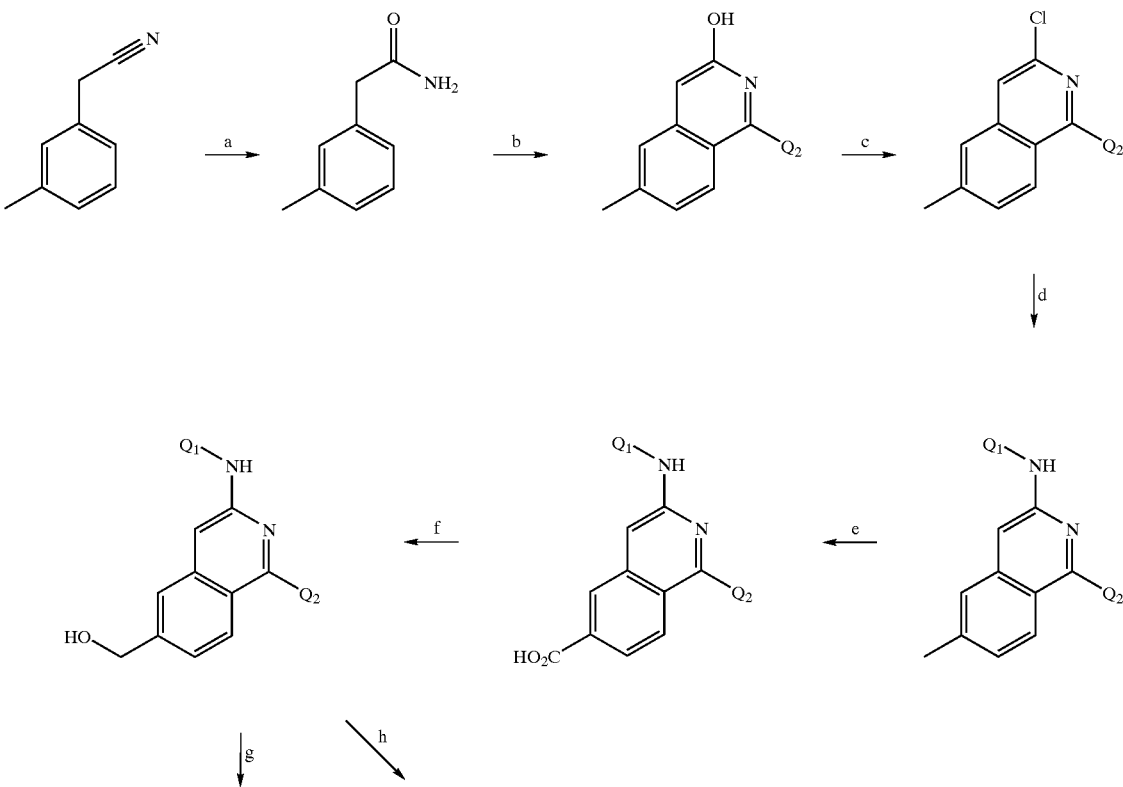

Scheme 7

37

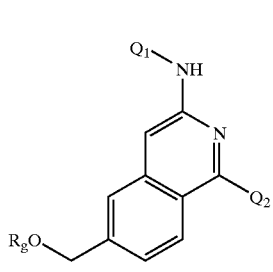

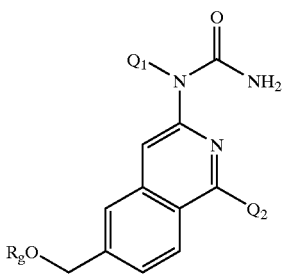

Conditions:
a) conc. $H_2SO_4$;
b) $Q_2CHO$, pTsOH, toluene;
c) $POCl_3$; d) $Q_1NH_2$, NaH, THF;
e) $KMnO_4$; f) $BH_3 \cdot DMS$;
g) $R_gBr$, $K_2CO_3$, THF; h) $MnO_2$;
i) $HN(R_h)_2$, $NaCNBH_3$;
j) $ClC(O)Cl$, $NH_4OH$.

38

-continued

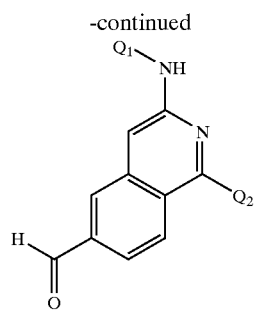

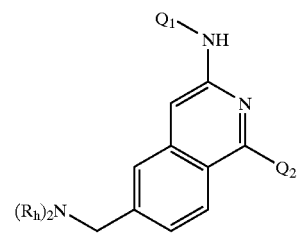

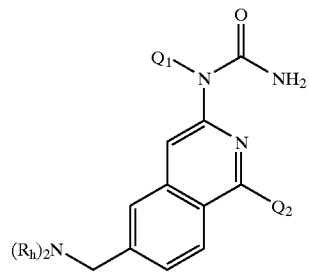

Scheme 7 may be used to synthesize compounds having the general formula of (Ic) or (Id) wherein Z=N and $R^3$ or $R^4$=$CH_2OR_g$ or $CH_2N(R_h)_2$. One having skill in the art will recognize unsymmetrical amine derivatives may also be used. Scheme 7 may be used to synthesize $CH_2$—O-linked or $CH_2$—N-linked $R^3$ and $R^4$ substituents.

Scheme 8

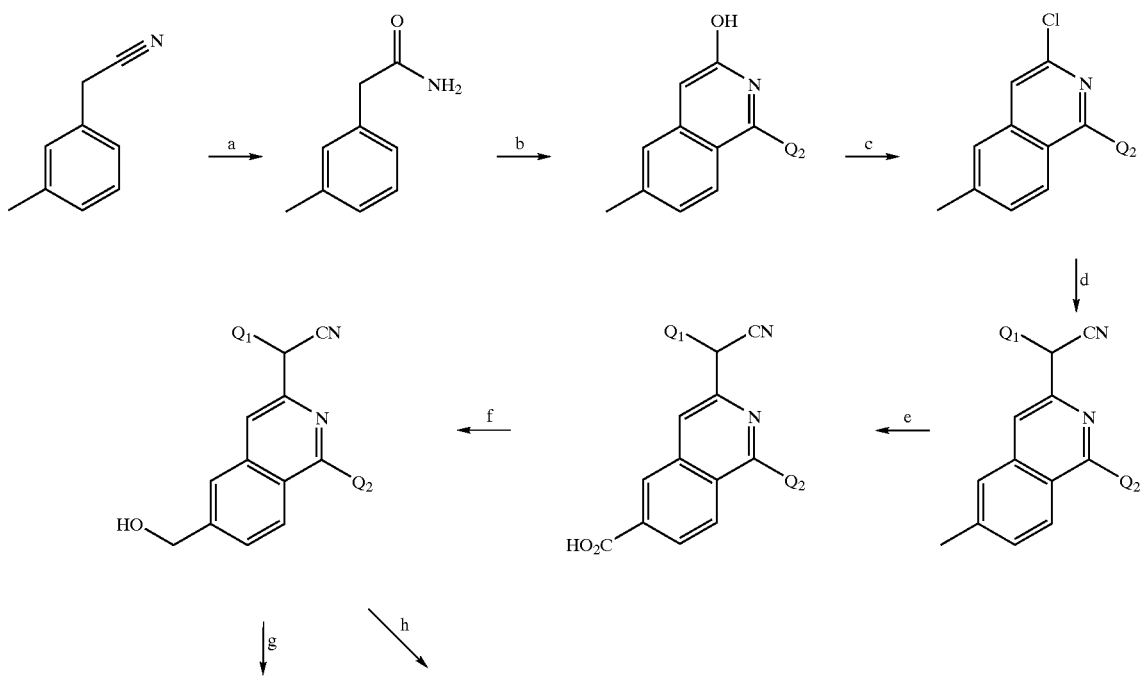

39

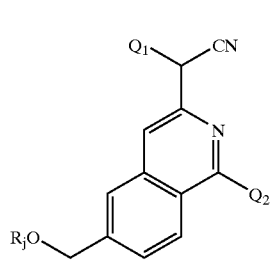

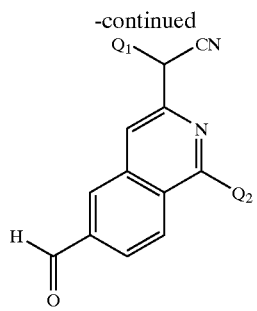

40

-continued

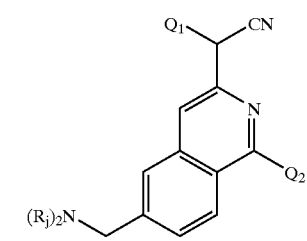

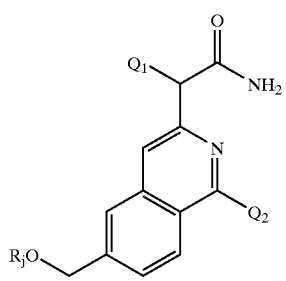

Conditions:
a) conc. H$_2$SO$_4$;
b) Q$_2$CHO, pTsOH, toluene;
c) POCl$_3$;  d) Q$_1$NH$_2$, NaH, THF;
e) KMnO$_4$;  f) BH$_3$•DMS;
g) R$_j$Br, K$_2$CO$_3$, THF;
h) MnO$_2$;  i) HN(R$_j$)$_2$, NaCNBH$_3$;
j) ClC(O)Cl, NH$_4$OH.

Scheme 8 may be used to synthesize compounds having the general formula of (Ic) or (Id) wherein Z=CH and R$^3$ or R$^4$=CH$_2$OR$_j$ or CH$_2$N(R$_j$)$_2$. One having skill in the art will recognize that unsymmetrical amine derivatives may also be used. Scheme 8 may be used to synthesize —CH$_2$—O-linked or —CH$_2$—N-linked R$^3$ and R$^4$ substituents.

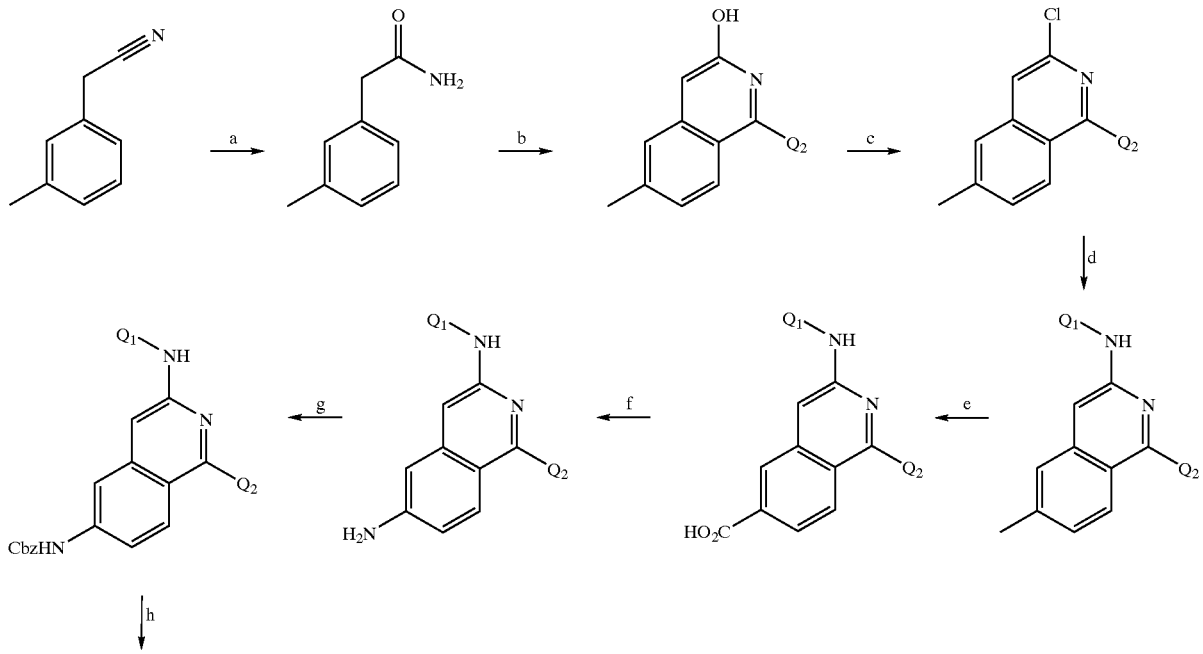

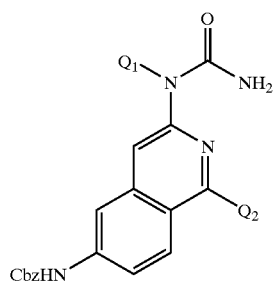
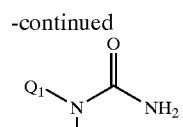
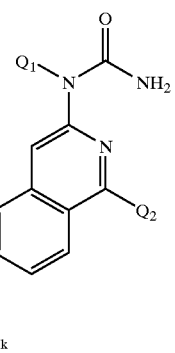
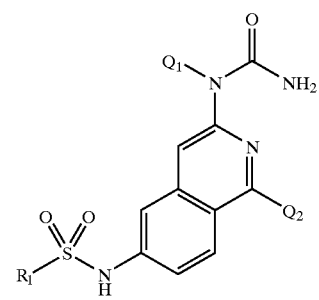
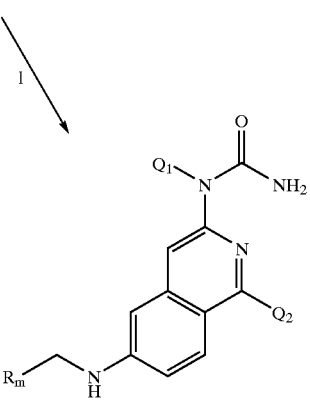

Conditions:
a) conc. $H_2SO_4$;  b) $Q_2CHO$, pTsOH, toluene;
c) $POCl_3$;  d) $Q_1NH_2$, NaH, THF;
e) $KMnO_4$;  f) $(PHO)_2PON_3$;
g) CbzCl, $Et_3N$, THF;  h) i. ClC(O)Cl, ii. $NH_4OH$;
i) $H_2$, 5% Pd/C;  j) $R_kCOCl$, $Et_3N$;
k) $R_lSO_2Cl$, $Et_3N$;  l) $R_mCHO$, $NaCNBH_3$.

Scheme 9 may be used to synthesize compounds having the general formula of (Ic) or (Id) wherein Z=N and $R^3$ or $R^4$=NHC(O)$R_k$, NHS(O)$_2R_l$ or NHCH$_2R_m$. Scheme 9 may be used to synthesize —NHC(O)-linked, NHS(O)$_2$-linked, or NHCH$_2$-linked $R^3$ and $R^4$ substituents.

Scheme 10

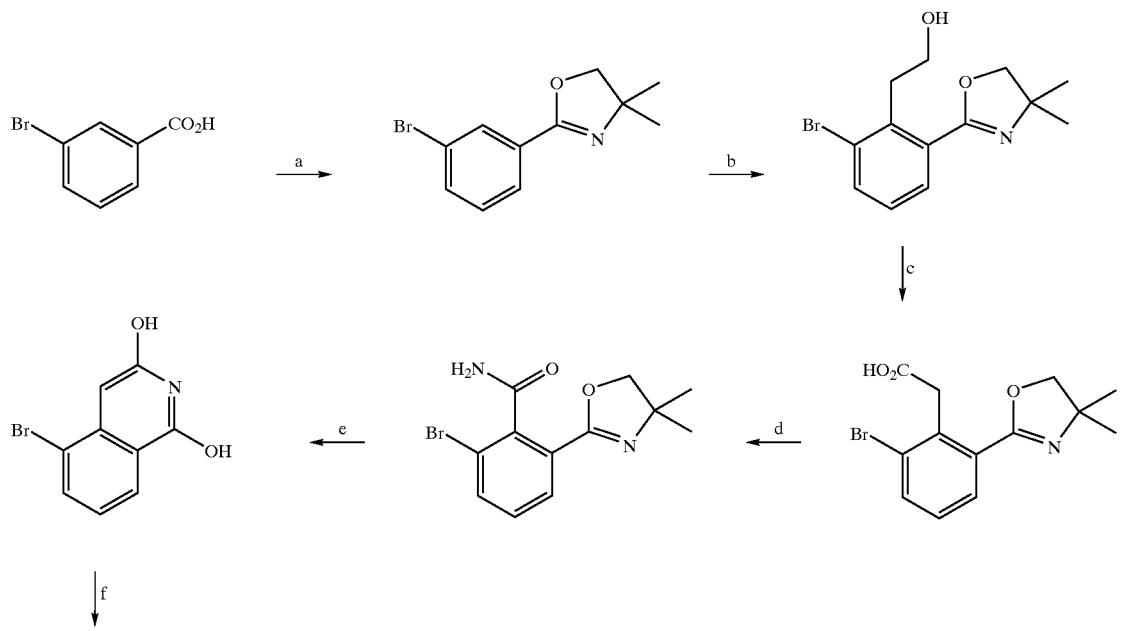

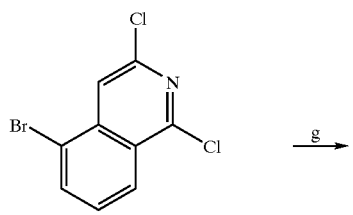
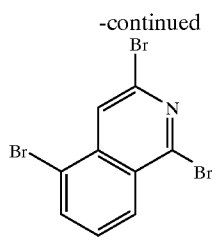

Conditions:
a) H$_2$NC(CH$_3$)CH2OH;
b) i. LDA, THF, ii. ethylene oxide;
c) NaClO$_2$;
d) i. ClC(O)C(OC)l, ii. NH$_4$OH;
e) 6N HCl;
f) POCl$_3$;
g) HBr, HOAc.

Scheme 10 may be used to synthesize compounds which can be further derivatized as in Scheme 11.

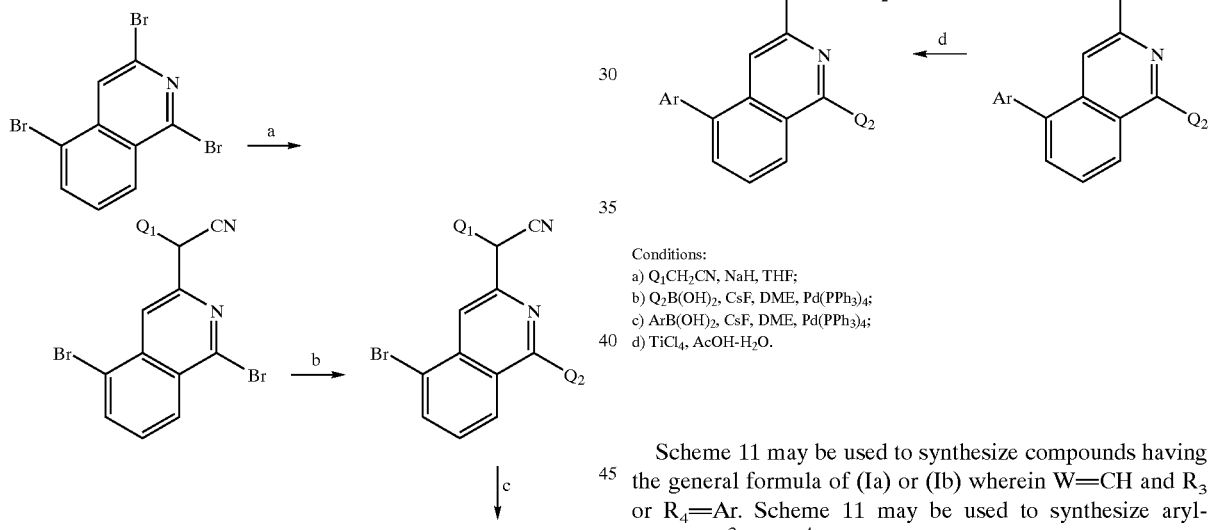

Conditions:
a) Q$_1$CH$_2$CN, NaH, THF;
b) Q$_2$B(OH)$_2$, CsF, DME, Pd(PPh$_3$)$_4$;
c) ArB(OH)$_2$, CsF, DME, Pd(PPh$_3$)$_4$;
d) TiCl$_4$, AcOH-H$_2$O.

Scheme 11 may be used to synthesize compounds having the general formula of (Ia) or (Ib) wherein W=CH and R$_3$ or R$_4$=Ar. Scheme 11 may be used to synthesize aryl-derived R$^3$ and R$^4$ substituents.

Scheme 12

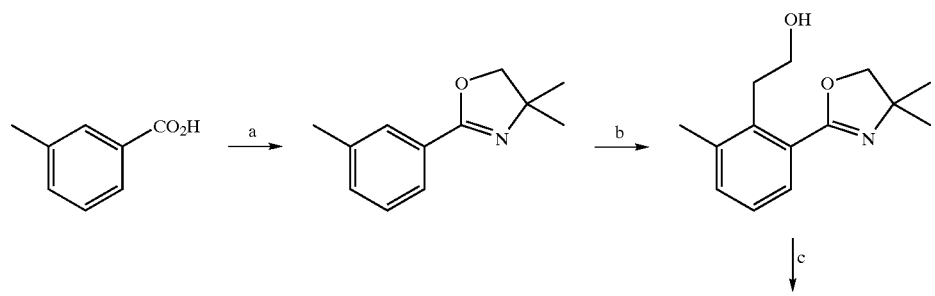

-continued
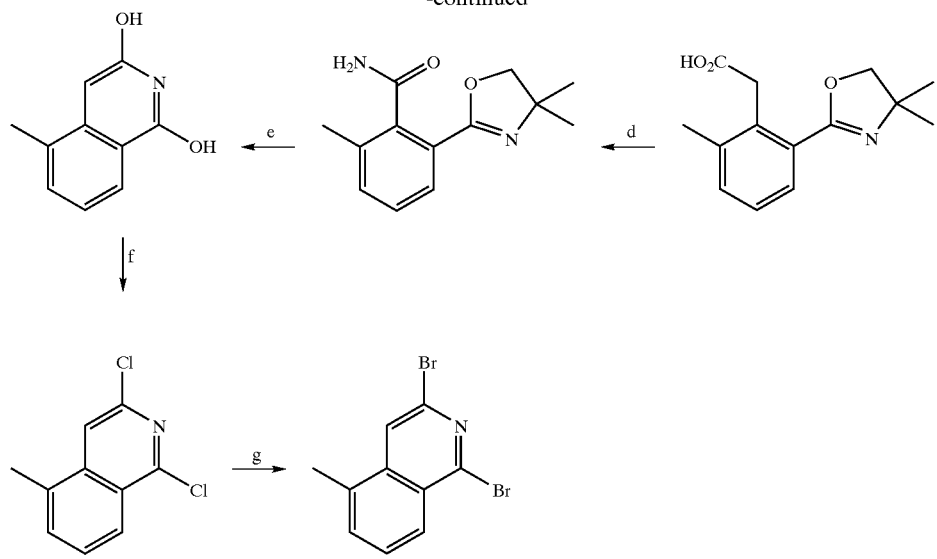
Conditions:
a) H₂NC(CH₃)CH₂OH;
b) i. LDA, THF, ii. ethylene oxide;
c) NaClO₂;
d) i. ClC(O)C(O)Cl, ii. NH₄OH;
e) 6N HCl;
f) POCl₃;
g) HBr, HOAc.
Scheme 12 may be used to synthesize compounds which can be further derivatized as in Schemes 13–15.
Scheme 13
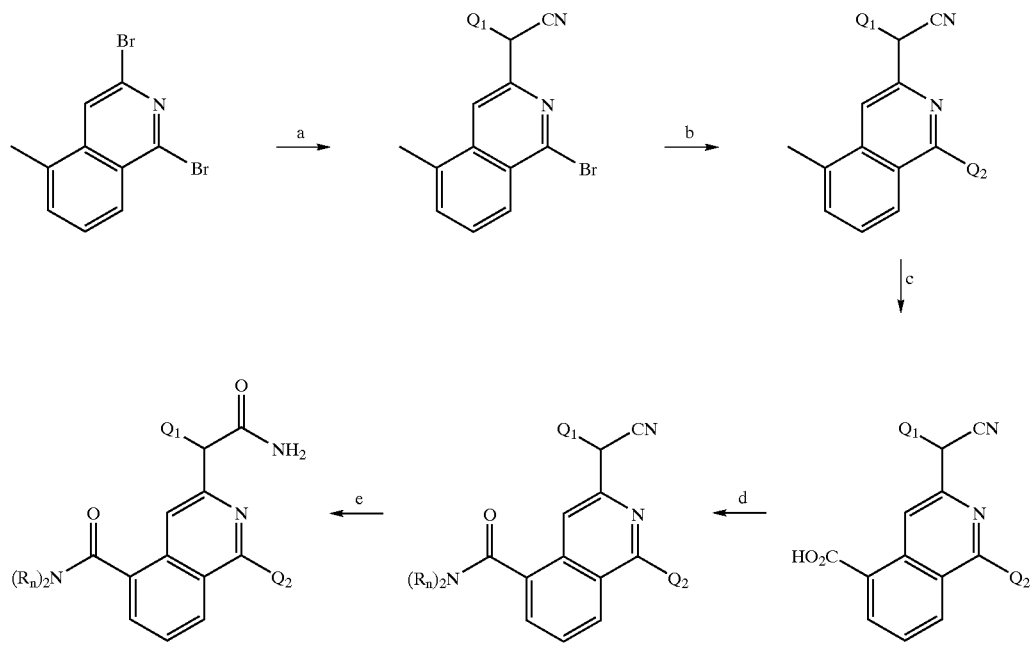
Conditions:
a) Q₁CH₂CN, NaH, THF;
b) Q₂B(OH)₂, CsF, DME, Pd(PPh₃)₄;
c) NaClO₂;
d) i. ClC(O)C(O)Cl, ii. HN(Rₙ)₂;
e) TiCl₄, AcOH-H₂O.

Scheme 13 may be used to synthesize compounds having the general formula of (Ia) or (Ib) wherein W=CH and $R^3$ or $R^4$=C(O)N($R_n$)$_2$. One having skill in the art will recognize that unsymmetrical amine derivatives may also be used. Scheme 13 may be used to synthesize C(O)N-linked $R^3$ and $R^4$ substituents.

Scheme 14 may be used to synthesize compounds having the general formula of (Ia) or (Ib) wherein W=CH and $R^3$ or $R^4$=CH$_2$O$R_p$ or CH$_2$N($R_q$)$_2$. One having skill in the art will recognize that unsymmetrical amine derivatives may be also be used. Scheme 14 may be used to synthesize —CH$_2$—O-linked or —CH$_2$—N-linked $R^3$ and $R^4$ substituents.

Scheme 14

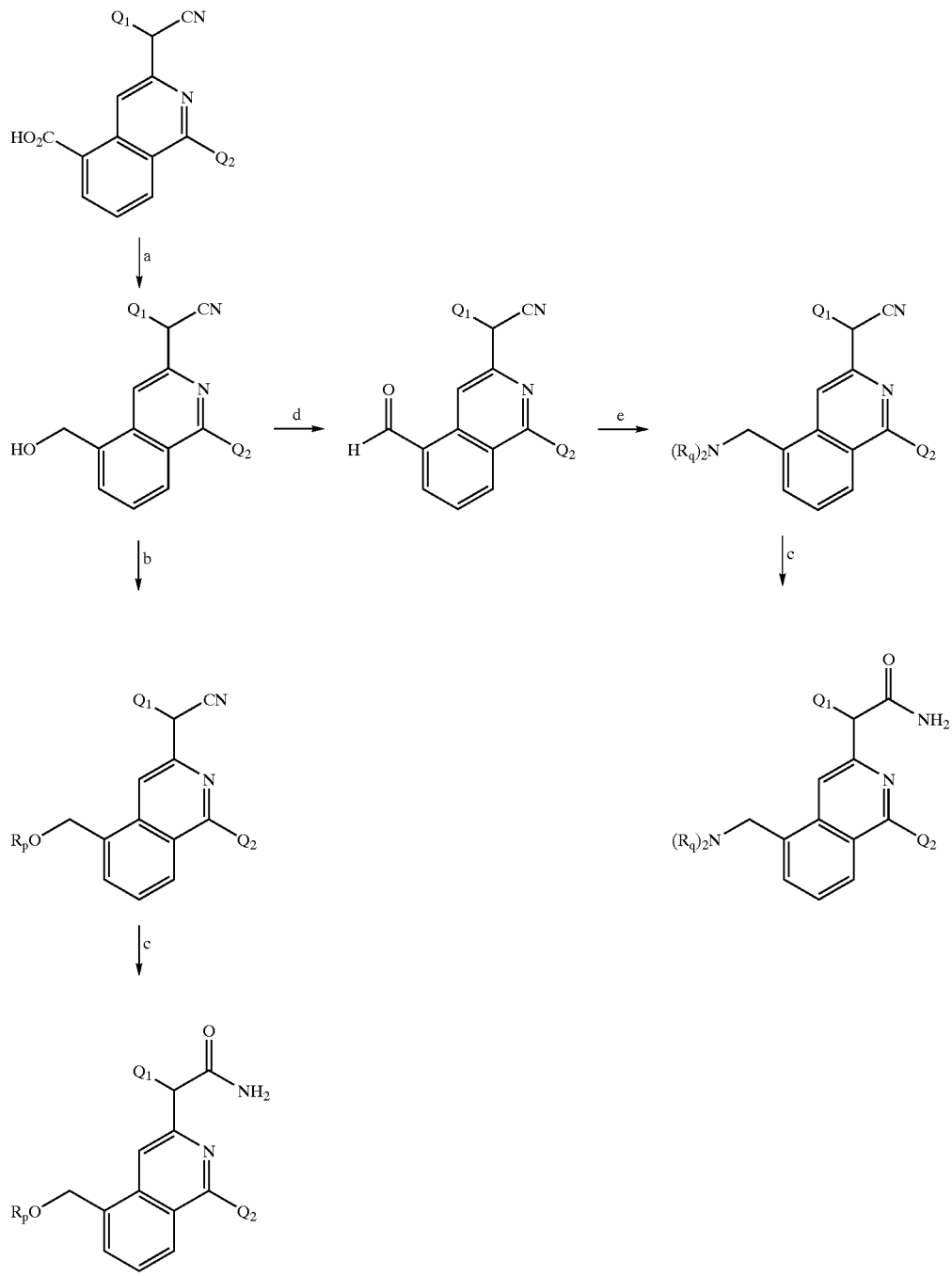

Conditions:
a) BH$_3$·DMS;
b) $R_p$Br, K$_2$CO$_3$, THF;
c) i. ClC(O)Cl, ii. NH$_4$OH;
d) MnO$_2$;
e) i. HN($R_q$)$_2$, ii. NaCNBH$_3$.

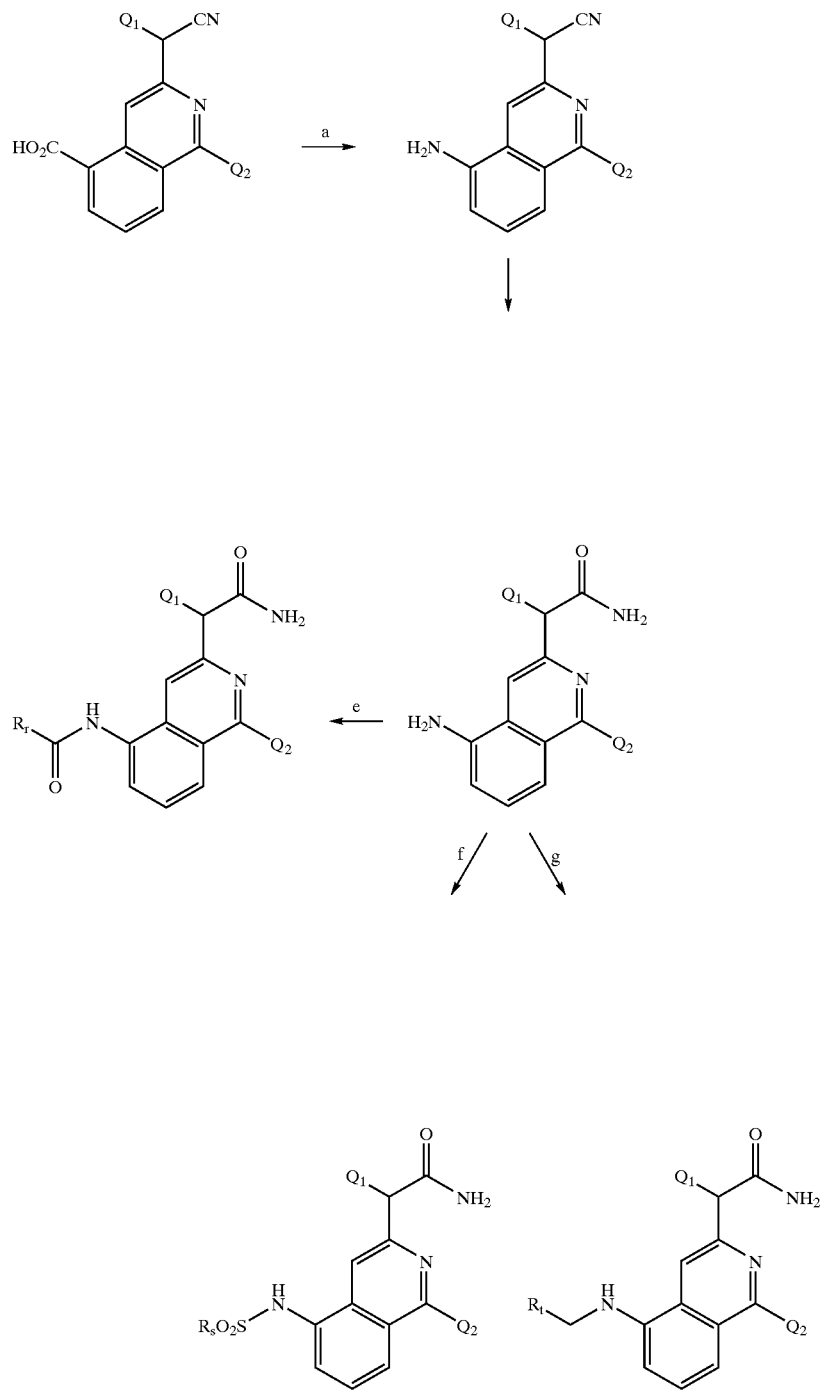
Conditions:
a) (PhO)₂PON₃;
b) CbzCl, Et₃N, THF;
c) i. ClC(O)Cl, ii. NH₄OH;
d) H₂, 5% Pd/C;
e) R$_r$COCl, Et₃N;
f) R$_s$SO₂Cl, Et₃N;
g) R$_t$CHO, NaCNBH₃.

Scheme 15 may be used to synthesize compounds having the general formula of (Ia) or (Ib) wherein W=CH and R³ or R⁴=NHC(O)R$_r$, NHSO$_2$R$_s$ or NHCH$_2$R$_t$. Scheme 15 may be used to synthesize —NHC(O)-linked, —NHSO$_2$-linked or —NHCH$_2$-linked R³ and R⁴ substituents.

It is a further embodiment of the present invention to provide compounds of the following formulae:

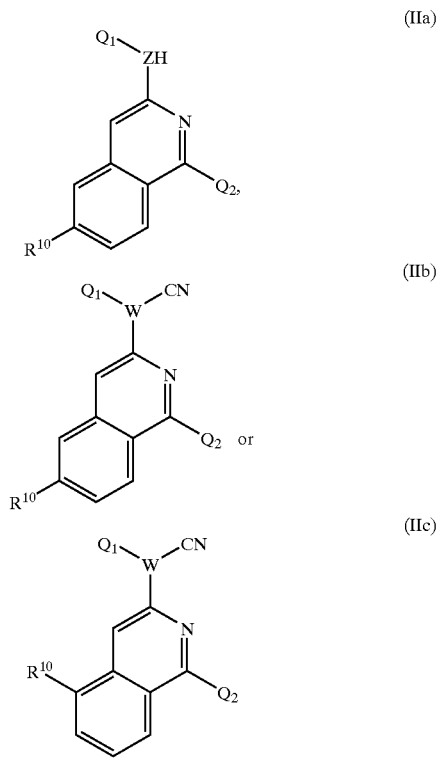

wherein R¹⁰ is R', R³, or R⁴;
and W, Z, Q$_1$, Q$_2$, R', R³ and R⁴ are as defined above. These compounds are useful, inter alia, as intermediates for preparation of compounds of formula Ia, Ib, Ic, and Id.

Preferred substituents for compounds IIa, IIb, and IIc are as described above for Ia, Ib, Ic, and Id.

According to another embodiment of the invention, the activity of the p38 inhibitors of this invention may be assayed in vitro, in vivo or in a cell line. In vitro assays include assays that determine inhibition of either the kinase activity or ATPase activity of activated p38. Alternate in vitro assays quantitate the ability of the inhibitor to bind to p38 and may be measured either by radiolabelling the inhibitor prior to binding, isolating the inhibitor/p38 complex and determining the amount of radiolabel bound, or by running a competition experiment where new inhibitors are incubated with p38 bound to known radioligands.

A compound of this invention preferably inhibits p38 protein kinase by at least 50% compared to the protein kinase alone in a standard assay, such as an assay described herein. In a preferred embodiment, the compounds inhibits the p38 kinase by at least 60%, more preferably 70%, even more preferably 80%, and yet more preferably 90%. In a still more preferred embodiment, the compounds of this invention inhibit p38 kinase activity by at leat 95% compared to the protein kinase alone.

Cell culture assays of the inhibitory effect of the compounds of this invention may determine the amounts of TNF, IL-1, IL-6 or IL-8 produced in whole blood or cell fractions thereof in cells treated with inhibitor as compared to cells treated with negative controls. Level of these cytokines may be determined through the use of commercially available ELISAs.

An in vivo assay useful for determining the inhibitory activity of the p38 inhibitors of this invention are the suppression of hind paw edema in rats with *Mycobacterium butyricum*-induced adjuvant arthritis. This is described in J. C. Boehm et al., J. Med. Chem., 39, pp. 3929–37 (1996), the disclosure of which is herein incorporated by reference. The p38 inhibitors of this invention may also be assayed in animal models of arthritis, bone resorption, endotoxin shock and immune function, as described in A. M. Badger et al., J. Pharmacol. Experimental Therapeutics, 279, pp. 1453–61 (1996), the disclosure of which is herein incorporated by reference.

The p38 inhibitors or pharmaceutical salts thereof may be formulated into pharmaceutical compositions for administration to animals or humans. These pharmaceutical compositions, which comprise an amount of p38 inhibitor effective to treat or prevent a p38-mediated condition and a pharmaceutically acceptable carrier, are another embodiment of the present invention.

The term "p38-mediated condition", as used herein means any disease or other deleterious condition in which p38 is known to play a role. This includes conditions known to be caused by IL-1, TNF, IL-6 or IL-8 overproduction. Such conditions include, without limitation, inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented by the compounds of this invention include, but are not limited to, acute pancreatitis, chronic pancreatitis, asthma, allergies, and adult respiratory distress syndrome.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented by the compounds of this invention include, but are not limited to, osteoporosis, osteoarthritis and multiple myeloma-related bone disorder.

Proliferative diseases which may be treated or prevented by the compounds of this invention include, but are not limited to, acute myelogenous leukemia, chronic myelogenous leukemia, metastatic melanoma, Kaposi's sarcoma, and multiple myeloma.

Angiogenic disorders which may be treated or prevented by the compounds of this invention include solid tumors, ocular neovasculization, infantile haemangiomas.

Infectious diseases which may be treated or prevented by the compounds of this invention include, but are not limited to, sepsis, septic shock, and Shigellosis.

Viral diseases which may be treated or prevented by the compounds of this invention include, but are not limited to, acute hepatitis infection (including hepatitis A, hepatitis B and hepatitis C), HIV infection and CMV retinitis.

Neurodegenerative diseases which may be treated or prevented by the compounds of this invention include, but are not limited to, Alzheimer's disease, Parkinson's disease, cerebral ischemias or neurodegenerative disease caused by traumatic injury.

"p38-mediated conditions" also include ischemia/reperfusion in stroke, heart attacks, myocardial ischemia, organ hypoxia, vascular hyperplasia, cardiac hypertrophy, and thrombin-induced platelet aggregation.

In addition, p38 inhibitors of the instant invention are also capable of inhibiting the expression of inducible pro-inflammatory proteins such as prostaglandin endoperoxide synthase-2 (PGHS-2), also referred to as cyclooxygenase-2 (COX-2). Therefore, other "p38-mediated conditions" which may be treated by the compounds of this invention include edema, analgesia, fever and pain, such as neuromuscular pain, headache, cancer pain, dental pain and arthritis pain.

The diseases that may be treated or prevented by the p38 inhibitors of this invention may also be conveniently grouped by the cytokine (IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes, pancreatic β-cell disease and Alzheimer's disease.

TNF-mediated disease or condition includes, rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and veterinary viral infections, such as lentivirus infections, including, but not limited to equine infectious anemia virus, caprine arthritis virus, visna virus or maedi virus; or retrovirus infections, including feline immunodeficiency virus, bovine immunodeficiency virus, or canine immunodeficiency virus.

IL-8 mediated disease or condition includes diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this invention may be used topically to treat or prevent conditions caused or exacerbated by IL-1 or TNF. Such conditions include inflamed joints, eczema, psoriasis, inflammatory skin conditions such as sunburn, inflammatory eye conditions such as conjunctivitis, pyresis, pain and other conditions associated with inflammation.

In addition to the compounds of this invention, pharmaceutically acceptable salts of the compounds of this invention may also be employed in compositions to treat or prevent the above-identified disorders.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium and potassium), alkaline earth metal (e.g., magnesium), ammonium and $N(C_{1-4} alkyl)_4^+$ salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partially glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of p38 inhibitor that may be combined with the carrier materials to produce a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a p38-mediated condition comprising the step of administering to a patient one of the above-described pharmaceutical compositions. The term "patient", as used herein, means an animal, preferably a human.

Preferably, that method is used to treat or prevent a condition selected from inflammatory diseases, autoimmune diseases, destructive bone disorders, proliferative disorders, infectious diseases, degenerative diseases, allergies, reperfusion/ischemia in stroke, heart attacks, angiogenic disorders, organ hypoxia, vascular hyperplasia, cardiac hypertrophy, and thrombin-induced platelet aggregation.

According to another embodiment, the inhibitors of this invention are used to treat or prevent an IL-1, IL-6, IL-8 or TNF-mediated disease or condition. Such conditions are described above.

Depending upon the particular p38-mediated condition to be treated or prevented, additional drugs, which are normally administered to treat or prevent that condition, may be administered together with the inhibitors of this invention. For example, chemotherapeutic agents or other anti-proliferative agents may be combined with the p38 inhibitors of this invention to treat proliferative diseases.

Those additional agents may be administered separately, as part of a multiple dosage regimen, from the p38 inhibitor-containing composition. Alternatively, those agents may be part of a single dosage form, mixed together with the p38 inhibitor in a single composition.

In order that the invention described herein may be more fully understood, the following examples are set forth. It should be understood that these examples are for illustrative purposes only and are not to be construed as limiting this invention in any manner.

EXAMPLE 1

Cloning of p38 Kinase in Insect Cells

Two splice variants of human p38 kinase, CSBP1 and CSBP2, have been identified. Specific oligonucleotide primers were used to amplify the coding region of CSBP2 cDNA using a HeLa cell library (Stratagene) as a template. The polymerase chain reaction product was cloned into the pET-15b vector (Novagen). The baculovirus transfer vector, pVL-(His)6-p38 was constructed by subcloning a XbaI-BamHI fragment of pET15b-(His)6-p38 into the complementary sites in plasmid pVL1392 (Pharmingen).

The plasmid pVL-(His)6-p38 directed the synthesis of a recombinant protein consisting of a 23-residue peptide (MGSSHHHHHHSSGLVPRGSHMLE, where LVPRGS represents a thrombin cleavage site) fused in frame to the N-terminus of p38, as confirmed by DNA sequencing and by N-terminal sequencing of the expressed protein. Monolayer culture of *Spodoptera frugiperda* (Sf9) insect cells (ATCC) was maintained in TNM-FH medium (Gibco BRL) supplemented with 10% fetal bovine serum in a T-flask at 27° C. Sf9 cells in log phase were co-transfected with linear viral DNA of *Autographa califonica* nuclear polyhedrosis virus (Pharmingen) and transfer vector pVL-(His)6-p38 using Lipofectin (Invitrogen). The individual recombinant baculovirus clones were purified by plaque assay using 1% low melting agarose.

EXAMPLE 2

Expression and Purification of Recombinant p38 Kinase

*Trichoplusia ni* (Tn-368) High-Five™ cells (Invitrogen) were grown in suspension in Excel-405 protein free medium (JRH Bioscience) in a shaker flask at 27° C. Cells at a density of $1.5 \times 10$ cells/ml were infected with the recombinant baculovirus described above at a multiplicity of infection of 5. The expression level of recombinant p38 was monitored by immunoblotting using a rabbit anti-p38 antibody (Santa Cruz Biotechnology). The cell mass was harvested 72 hours after infection when the expression level of p38 reached its maximum.

Frozen cell paste from cells expressing the $(His)_6$-tagged p38 was thawed in 5 volumes of Buffer A (50 mM $NaH_2PO_4$ pH 8.0, 200 mM NaCl, 2 mM β-Mercaptoethanol, 10% Glycerol and 0.2 mM PMSF). After mechanical disruption of the cells in a microfluidizer, the lysate was centrifuged at 30,000×g for 30 minutes. The supernatant was incubated batchwise for 3–5 hours at 4° C. with Talon™ (Clontech) metal affinity resin at a ratio of 1 ml of resin per 2–4 mgs of expected p38. The resin was settled by centrifugation at 500×g for 5 minutes and gently washed batchwise with Buffer A. The resin was slurried and poured into a column (approx. 2.6×5.0 cm) and washed with Buffer A+5 mM imidazole.

The $(His)_6$-p38 was eluted with Buffer A+100 mM imidazole and subsequently dialyzed overnight at 4° C. against 2 liters of Buffer B, (50 mM HEPES, pH 7.5, 25 mM β-glycerophosphate, 5% glycerol, 2 mM DTT). The $His_6$ tag was removed by addition of at 1.5 units thrombin (Calbiochem) per mg of p38 and incubation at 20° C. for 2–3 hours. The thrombin was quenched by addition of 0.2 mM PMSF and then the entire sample was loaded onto a 2 ml benzamidine agarose (American International Chemical) column.

The flow through fraction was directly loaded onto a 2.6×5.0 cm Q-Sepharose (Pharmacia) column previously equilibrated in Buffer B+0.2 mM PMSF. The p38 was eluted with a 20 column volume linear gradient to 0.6M NaCl in Buffer B. The eluted protein peak was pooled and dialyzed overnight at 4° C. vs. Buffer C (50 mM HEPES pH 7.5, 5% glycerol, 50 mM NaCl, 2 mM DTT, 0.2 mM PMSF).

The dialyzed protein was concentrated in a Centriprep (Amicon) to 3–4 ml and applied to a 2.6×100 cm Sephacryl S-100HR (Pharmacia) column. The protein was eluted at a flow rate of 35 ml/hr. The main peak was pooled, adjusted to 20 mM DTT, concentrated to 10–80 mgs/ml and frozen in aliquots at −70° C. or used immediately.

EXAMPLE 3

Activation of p38 p38 was activated by combining 0.5 mg/ml p38 with 0.005 mg/ml DD-double mutant MKK6 in Buffer B+10 mM $MgCl_2$, 2 mM ATP, 0.2 mM $Na_2VO_4$ for 30 minutes at 20° C. The activation mixture was then loaded onto a 1.0×10 cm MonoQ column (Pharmacia) and eluted with a linear 20 column volume gradient to 1.0 M NaCl in Buffer B. The activated p38 eluted after the ADP and ATP. The activated p38 peak was pooled and dialyzed against buffer B+0.2 mM $Na_2VO_4$ to remove the NaCl. The dialyzed protein was adjusted to 1.1M potassium phosphate by addition of a 4.0M stock solution and loaded onto a 1.0×10 cm HIC (Rainin Hydropore) column previously equilibrated in Buffer D (10% glycerol, 20 mM β-glycerophosphate, 2.0 mM DTT)+ 1.1M$K_2HPO_4$. The protein was eluted with a 20 column volume linear gradient to Buffer D+50 mM $K_2HPO_4$. The double phosphorylated p38 eluted as the main peak and was pooled for dialysis against Buffer B+0.2 mM $Na_2VO_4$. The activated p38 was stored at −70° C.

EXAMPLE 4 p38 Inhibition Assays

A. Inhibition of Phosphorylation of EGF Receptor Peptide

This assay is carried out in the presence of 10 mM $MgCl_2$, 25 mM β-glycerophosphate, 10% glycerol and 100 mM HEPES buffer at pH 7.6. For a typical $IC_{50}$ determination, a stock solution is prepared containing all of the above components and activated p38 (5 nM). The stock solution is aliquotted into vials. A fixed volume of DMSO or inhibitor in DMSO (final concentration of DMSO in reaction was 5%) is introduced to each vial, mixed and incubated for 15 minutes at room temperature. EGF receptor peptide, KRELVEPLTPSGEAPNQALLR, a phosphoryl acceptor in p38-catalyzed kinase reaction (1), is added to each vial to a final concentration of 200 μM. The kinase reaction is initiated with ATP (100 μM) and the vials are incubated at 30° C. After 30 minutes, the reactions are quenched with equal volume of 10% trifluoroacetic acid (TFA).

The phosphorylated peptide is quantified by HPLC analysis. Separation of phosphorylated peptide from the unphosphorylated peptide is achieved on a reverse phase column (Deltapak, 5 μm, C18 100D, Part no. 011795) with a binary gradient of water and acteonitrile, each containing 0.1% TFA. $IC_{50}$ (concentration of inhibitor yielding 50% inhibition) is determined by plotting the percent (%) activity remaining against inhibitor concentration.

B. Inhibition of ATPase Activity

This assay is carried out in the presence of 10 mM $MgCl_2$, 25 mM β-glycerophosphate, 10% glycerol and 100 mM HEPES buffer at pH 7.6. For a typical Ki determination, the Km for ATP in the ATPase activity of activated p38 reaction is determined in the absence of inhibitor and in the presence of two concentrations of inhibitor. A stock solution is prepared containing all of the above components and activated p38 (60 nM). The stock solution is aliquotted into vials. A fixed volume of DMSO or inhibitor in DMSO (final concentration of DMSO in reaction was 2.5%) is introduced to each vial, mixed and incubated for 15 minutes at room temperature. The reaction is initiated by adding various concentrations of ATP and then incubated at 30° C. After 30 minutes, the reactions are quenched with 50 μl of EDTA (0.1 M, final concentration), pH 8.0. The product of p38 ATPase activity, ADP, is quantified by HPLC analysis.

Separation of ADP from ATP is achieved on a reversed phase column (Supelcosil, LC-18, 3 μm, part no. 5-8985) using a binary solvent gradient of following composition: Solvent A—0.1 M phosphate buffer containing 8 mM tetrabutylammonium hydrogen sulfate (Sigma Chemical Co., catalogue no. T-7158), Solvent B-Solvent A with 30% methanol.

Ki is determined from the rate data as a function of inhibitor and ATP concentrations.

p38 inhibitors of this invention will inhibit the ATPase activity of p38.

C. Inhibition of IL-1, TNF, IL-6 and IL-8 Production in LPS-Stimulated PBMCs

Inhibitors are serially diluted in DMSO from a 20 mM stock. At least 6 serial dilutions are prepared. Then 4× inhibitor stocks are prepared by adding 4 μl of an inhibitor dilution to 1 ml of RPMI1640 medium/10% fetal bovine serum. The 4× inhibitor stocks contained inhibitor at concentrations of 80 μM, 32 μM, 12.8 μM, 5.12 μM, 2.048 μM, 0.819 μM, 0.328 μM, 0.131 μM, 0.052 μM, 0.021 μM etc. The 4× inhibitor stocks are pre-warmed at 37° C. until use.

Fresh human blood buffy cells are separated from other cells in a Vacutainer CPT from Becton & Dickinson (containing 4 ml blood and enough DPBS without $Mg^{2+}$/$Ca^{2+}$ to fill the tube) by centrifugation at 1500×g for 15 min. Peripheral blood mononuclear cells (PBMCs) located on top of the gradient in the Vacutainer, are removed and washed twice with RPMI1640 medium/10% fetal bovine serum. PBMCs are collected by centrifugation at 500×g for 10 min. The total cell number is determined using a Neubauer Cell Chamber and the cells are adjusted to a concentration of $4.8×10^6$ cells/ml in cell culture medium (RPMI1640 supplemented with 10% fetal bovine serum).

Alternatively, whole blood containing an anti-coagulant is used directly in the assay.

100 μl of cell suspension or whole blood are placed in each well of a 96-well cell culture plate. Then 50 μl of the 4× inhibitor stock is added to the cells. Finally, 50 μl of a lipopolysaccharide (LPS) working stock solution (16 ng/ml in cell culture medium) is added to give a final concentration of 4 ng/ml LPS in the assay. The total assay volume of the vehicle control is also adjusted to 200 μl by adding 50 μl cell culture medium. The PBMC cells or whole blood are then incubated overnight (for 12–15 hours) at 37° C./5% $CO_2$ in a humidified atmosphere.

The next day the cells are mixed on a shaker for 3–5 minutes before centrifugation at 500×g for 5 minutes. Cell culture supernatants are harvested and analyzed by ELISA for levels of IL-1β (R & D Systems, Quantikine kits, #DBL50), TNF-α (BioSource, #KHC3012), IL-6 (Endogen, #EH2-IL6) and IL-8 (Endogen, #EH2-IL8) according to the instructions of the manufacturer. The ELISA data are used to generate dose-response curves from which IC50 values were derived.

Other p38 inhibitors of this invention will also inhibit phosphorylation of EGF receptor peptide, and will inhibit the production of IL-1, TNF and IL-6, as well as IL-8, in LPS-stimulated PBMCs or in whole blood.

D. Inhibition of IL-6 and IL-8 Production in IL-1-Stimulated PBMCs

This assay is carried out on PBMCs exactly the same as above except that 50 μl of an IL-1b working stock solution (2 ng/ml in cell culture medium) is added to the assay instead of the (LPS) working stock solution.

Cell culture supernatants are harvested as described above and analyzed by ELISA for levels of IL-6 (Endogen, #EH2-IL6) and IL-8 (Endogen, #EH2-IL8) according to the instructions of the manufacturer. The ELISA data are used to generate dose-response curves from which IC50 values are derived.

E. Inhibition of LPS-Induced Prostaglandin Endoperoxide Synthase-2 (PGHS-2, or COX-2) Induction in PBMCs Human peripheral mononuclear cells (PBMCs) are isolated from fresh human blood buffy coats by centrifugation in a Vacutainer CPT (Becton & Dickinson). $15×10^6$ cells are seeded in a 6-well tissue culture dish containing RPMI 1640 supplemented with 10% fetal bovine serum, 50 U/ml penicillin, 50 μg/ml streptomycin, and 2 mM L-glutamine. Compounds are added at 0.2, 2.0 and 20 μM final concentrations in DMSO. LPS is then added at a final concentration of 4 ng/ml to induce enzyme expression. The final culture volume is 10 ml/well.

After overnight incubation at 37° C., 5% $CO_2$, the cells are harvested by scraping and subsequent centrifugation, the supernatant is removed, and the cells are washed twice in ice-cold DPBS (Dulbecco's phosphate buffered saline, BioWhittaker). The cells are lysed on ice for 10 min in 50 μl cold lysis buffer (20 mM Tris-HCl, pH 7.2, 150 mM NaCl, 1% Triton-X-100, 1% deoxycholic acid, 0.1% SDS, 1 mM EDTA, 2% aprotinin (Sigma), 10 μg/ml pepstatin, 10 μg/ml leupeptin, 2 mM PMSF, 1 mM benzamidine, 1 mM DTT) containing 1 μl Benzonase (DNAse from Merck). The protein concentration of each sample is determined using the BCA assay (Pierce) and bovine serum albumin as a standard. Then the protein concentration of each sample is adjusted to 1 mg/ml with cold lysis buffer. To 100 μl lysate an equal volume of 2×SDS PAGE loading buffer is added and the sample is boiled for 5 min. Proteins (30 μg/lane) are size-fractionated on 4–20% SDS PAGE gradient gels (Novex) and subsequently transferred onto nitrocellulose membrane by electrophoretic means for 2 hours at 100 mA in Towbin transfer buffer (25 mM Tris, 192 mM glycine) containing 20% methanol. After transfer, the membrane is pretreated for 1 hour at room temperature with blocking buffer (5% non-fat dry milk in DPBS supplemented with 0.1% Tween-20) and washed 3 times in DPBS/0.1% Tween-20. The membrane is incubated overnight at 4° C. with a 1:250 dilution of monoclonal anti-COX-2 antibody (Transduction Laboratories) in blocking buffer. After 3 washes in DPBS/0.1% Tween-20, the membrane is incubated with a 1:1000 dilution of horseradish peroxidase-conjugated sheep antiserum to mouse Ig (Amersham) in blocking buffer for 1 h at room temperature. Then the membrane is washed again 3 times in DPBS/0.1% Tween-20. An ECL detection system (SuperSignal™ CL-HRP Substrate System, Pierce) is used to determine the levels of expression of COX-2.

While we have hereinbefore presented a number of embodiments of this invention, it is apparent that our basic construction can be altered to provide other embodiments which utilize the methods of this invention.

We claim:

1. A compound of the formula:

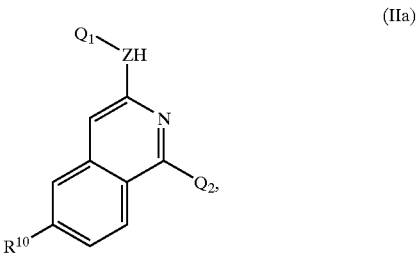

(IIa)

-continued

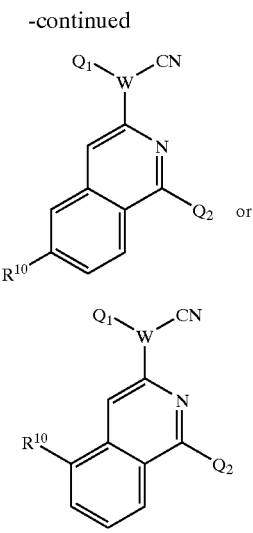

(IIb)

or (IIc)

wherein each of $Q_1$ and $Q_2$ are;

the rings that make up $Q_1$ are substituted with 1 to 4 substituents, each of which is independently selected from halo; $C_1$–$C_3$ aliphatic optionally substituted with halo, R', N(R')$_2$, OR', CO$_2$R' or CON(R')$_2$; O—(C$_1$–C$_3$)-aliphatic optionally substituted with halo, R', N(R')$_2$, OR', CO$_2$R' or CON(R')$_2$; R'; N(R')$_2$; OCF$_3$; CF$_3$; NO$_2$; CO$_2$R'; CON(R')$_2$; SR'; S(O$_2$)N(R')$_2$; SCF$_3$; CN; N(R')C(O)R$^4$; N(R')C(O)OR$^4$; N(R')C(O)C(O)R$^4$; N(R')S(O$_2$)R$^4$; N(R')R$^4$; N(R$^4$)$_2$; OR$^4$; OC(O)R$^4$; OP(O)$_3$H$_2$; N=CR'—N(R')$_2$; SO$_2$R'; or C(O)R';

the rings that make up $Q_2$ are optionally substituted with up to 4 substituents, each of which is independently selected from halo; $C_1$–$C_3$ aliphatic optionally substituted with halo, R', N(R')$_2$, OR', CO$_2$R', S(O$_2$)N(R')$_2$, N=CR'—N(R')$_2$, R$^3$, O—P(O$_3$)H$_2$, or CON(R')$_2$; O—(C$_1$–C$_3$)-aliphatic optionally substituted with halo, R', N(R')$_2$, OR', CO$_2$R', S(O$_2$)N(R')$_2$, N=CR'—N(R')$_2$, R$^3$, OP(O$_3$)H$_2$, or CON(R')$_2$; R'; N(R')$_2$; OCF$_3$; CF$_3$; NO$_2$; CO$_2$R'; CON(R')$_2$; R$^3$; OR$^3$; N(R$^3$)$_2$; SR$^3$; C(O)R$^3$; C(O)N(R')R$^3$; C(O)OR$^3$; SR'; S(O$_2$)N(R')$_2$; SCF$_3$; N=CR'—N(R')$_2$; R$^4$; O—CO$_2$R$^4$; N(R')C(O)R$^4$; N(R')C(O)OR$^4$; N(R')C(O)C(O)R$^4$; N(R')S(O$_2$)R$^4$; N(R')R$^4$; N(R$^4$)$_2$; OR$^4$; OC(O)R$^4$; OP(O)$_3$H$_2$; or CN;

each R' is independently selected from hydrogen; (C$_1$–C$_3$)-aliphatic; phenyl or phenyl substituted with 1 to 3 substituents independently selected from halo, methoxy, cyano, nitro, amino, hydroxy, methyl or ethyl; or a 5–8 membered heterocyclic ring system optionally substituted with 1 to 3 substituents independently selected from halo, methoxy, cyano, nitro, amino, hydroxy, methyl or ethyl;

each R$^3$ is independently selected from a 5–8 membered aromatic or non-aromatic carbocyclic or heterocyclic ring system each optionally substituted with halo, R', R$^4$, —C(O)R', —C(O)R$^4$, —C(O)OR$^4$, —J or —K; or an 8–10 membered saturated, partially unsaturated, or aromatic bicyclic ring system containing 0–4 heteroatoms, said ring system optionally substituted with halo, R', R$^4$, —C(O)R', —C(O)R$^4$, —C(O)OR$^4$, —J or —K;

each R$^4$ is independently selected from —N(R')$_2$; —NR'C(O)—(C$_1$–C$_4$)-aliphatic optionally substituted with halo, R', N(R')$_2$, OR', CO$_2$R', CON(R')$_2$, SO$_2$N(R')$_2$, SO$_2$N(R$^5$)$_2$, —J or —K; —NR''(C$_1$–C$_4$)-aliphatic optionally substituted with halo, R', N(R')$_2$, OR', CO$_2$R', CON(R')$_2$, SO$_2$N(R')$_2$, SO$_2$N(R$^5$)$_2$, —J or —K; —OC(O)—N(R')$_2$; (C$_1$–C$_4$)-aliphatic, wherein up to two saturated carbon atoms of the aliphatic chain are each optionally and independently replaced by —C(O)—, —C(O)NR'—, —C(O)NR'NR'—, —CO$_2$—, —NR'C(O)NR'—, —OC(O)—, C(O)C(O)—, —OC(O)NR'—, —NR'NR'—, —NR'CO—, —NR'O—, —O—, —S—, —SO—, —SO$_2$—, —NR'—, —SO$_2$NR'—, —NR'SO$_2$—, and wherein the aliphatic chain is optionally substituted with halo, R', N(R')$_2$, OR', CO$_2$R', CON(R')$_2$, SO$_2$N(R')$_2$, SO$_2$N(R$^5$)$_2$, —J or —K; a (C$_1$–C$_7$)-aliphatic optionally substituted with halo, R', N(R')$_2$, OR', CO$_2$R', CON(R')$_2$, SO$_2$N(R')$_2$, SO$_2$N(R$^5$)$_2$, —J or —K; —J; —K; or a 5–6 membered aromatic or non-aromatic carbocyclic or heterocyclic ring system optionally substituted with halo, R', N(R')$_2$, OR', CO$_2$R', C(O)N(R')$_2$, SO$_2$N(R')$_2$ SO$_2$N(R$^5$)$_2$, —J or —K;

R$^5$ is selected from hydrogen; or a (C$_1$–C$_3$)-aliphatic optionally substituted with halo, —R', —N(R')$_2$, —OR', SR', —C(O)N(R')$_2$, —S(O)$_2$N(R')$_2$, —C(O)OR', —N(R')S(O)$_2$(R'), —N(R')SO$_2$R$^6$, —C(O)N(R')(R$^6$), —N(R')C(O)R', —N(R')(R$^6$), —C(O)R$^6$, —C(O)N=C(NHR')$_2$ or R$^6$;

R$^6$ is selected from 5–8 membered aromatic or non-aromatic carbocyclic or heterocyclic ring systems each optionally substituted with halo, R', —C(O)R' or —C(O)OR'; or an 8–10 membered saturated, partially unsaturated, or aromatic ring system containing 0–4 heteroatoms, said ring system optionally substituted with halo, R', —C(O)R' or C(O)OR';

Z is N, CH, C(OCH$_3$), C(CH$_3$), C(NH$_2$), C(OH) or C(F);

W is CH, C(OCH$_3$), C(CH$_3$), C(NH$_2$), C(OH) or C(F);

J is T or is a (C$_1$–C$_4$) aliphatic substituted with T;

T is V, O(V) or NH(V);

V is C(O)N=C(R)(N(R)$_2$) wherein the two geminal R on the nitrogen are optionally taken together with the nitrogen to form a 4–8 membered heterocyclic ring;

each R is independently selected from hydrogen, —R$^2$, —N(R$^2$)$_2$, —OR$^2$, SR$^2$, —C(O)N(R$^2$)$_2$, —S(O$_2$)N(R$^2$)$_2$, —C(O)OR$^2$ or —C(O)R$^2$ wherein two adjacent R are optionally bound to one another and, together with each C or N to which they are respectively bound, form a 4–8 membered carbocyclic or heterocyclic ring;

R$^2$ is selected from hydrogen; or a (C$_1$–C$_3$)-aliphatic optionally substituted with halo, —R', —N(R')$_2$, —OR', SR', —C(O)N(R')$_2$, —S(O$_2$)N(R')$_2$, —C(O)OR', —N(R')SO$_2$R$^8$, —N(R')SO$_2$R$^7$, —C(O)N(R')(R$^7$), —N(R')C(O)R$^8$, —N(R')(R$^7$), —N(R')(R$^8$), —C(O)R$^7$, —C(O)N(R')(R$^8$), —N(R$^8$)$_2$, —C(O)N=C(NHR')$_2$ or R$^7$;

R$^7$ is selected from 5–8 membered aromatic or non-aromatic carbocyclic or heterocyclic ring systems each optionally substituted with halo, R', R$^8$, —C(O)R', —C(O)R$^8$, —C(O)OR$^8$; or an 8–10 membered saturated, partially unsaturated, or aromatic bicyclic ring system containing 0–4 heteroatoms, said ring system optionally substituted with halo, R', $R^8$, —C(O)R', —C(O)$R^8$, or —C(O)O$R^8$;

$R^8$ is selected from $C_1$–$C_4$ aliphatic, wherein up to two saturated carbon atoms of the aliphatic chain are each optionally and independently replaced by —C(O)—, —C(O)NR'—, —C(O)NR'NR'—, —$CO_2$—, —NR'C(O)NR'—, —OC(O)—, —C(O)C(O)—, —OC(O)NR'—, —NR'NR'—, —NR'CO—, —NR'O—, —O—, —S—, —SO—, —$SO_2$—, —NR'—, —$SO_2$NR'—, —NR'$SO_2$—, and wherein the aliphatic chain is optionally substituted with halo, R', N(R')$_2$, OR', $CO_2$R', CON(R')$_2$, $SO_2$N(R')$_2$, $SO_2$N($R^5$)$_2$; a ($C_1$–$C_7$)-aliphatic optionally substituted with halo, R', N(R')$_2$, OR', $CO_2$R', CON(R')$_2$, $SO_2$N(R')$_2$, $SO_2$N($R^5$)$_2$; or a 5–6 membered carbocyclic or heterocyclic ring system optionally substituted with halo, R', N(R')$_2$, OR', $CO_2$R', C(O)N(R')$_2$, $SO_2$N(R')$_2$, or $SO_2$N($R^5$)$_2$;

K is —C(O)—D, a ($C_1$–$C_4$) aliphatic substituted with D or —OP(O)(OH)$_2$;

D is

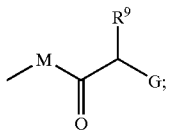

M is either O or NH;

G is selected from $NH_2$, OH, or H;

$R^9$ is H; OH; C(O)OH; ($C_0$–$C_7$)-aliphatic optionally substituted with halo, R', N(R')$_2$, OR', $CO_2$R', CON(R')$_2$, or $SO_2$N(R')$_2$; or a 5–6 membered carbocyclic or heterocyclic ring system optionally substituted with halo, R', N(R')$_2$, OR', $CO_2$R', C(O)N(R')$_2$, or $SO_2$N(R')$_2$; or G and $R^9$ taken together with the intervening carbon may form a ring; and $R^{10}$ is R', $R^3$, or $R^4$.

* * * * *

UNITED STATES PATENT AND TRADEMARK OFFICE
CERTIFICATE OF CORRECTION

| | |
|---|---|
| PATENT NO. | : 6,759,535 B2 |
| APPLICATION NO. | : 10/400269 |
| DATED | : July 6, 2004 |
| INVENTOR(S) | : Cochran et al. |

It is certified that error appears in the above-identified patent and that said Letters Patent is hereby corrected as shown below:

Column 63, line 23: Insert --phenyl-- after "$Q_1$ and $Q_2$ are".

Column 64, line 4: Change "—NR"" to -—NR'--.

Column 66, line 12: Change "$(C_0-C_7)$" to --$(C_1-C_7)$--.

Signed and Sealed this

Twenty-second Day of August, 2006

JON W. DUDAS
*Director of the United States Patent and Trademark Office*